(12) United States Patent
Wales et al.

(10) Patent No.: US 7,213,736 B2
(45) Date of Patent: May 8, 2007

(54) SURGICAL STAPLING INSTRUMENT INCORPORATING AN ELECTROACTIVE POLYMER ACTUATED FIRING BAR TRACK THROUGH AN ARTICULATION JOINT

(75) Inventors: Kenneth S. Wales, Mason, OH (US); Frederick E. Shelton, IV, Hillsboro, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 82 days.

(21) Appl. No.: 11/083,740

(22) Filed: Mar. 18, 2005

(65) Prior Publication Data

US 2005/0165415 A1 Jul. 28, 2005

Related U.S. Application Data

(63) Continuation-in-part of application No. 10/615,971, filed on Jul. 9, 2003, now Pat. No. 6,964,363.

(60) Provisional application No. 60/591,694, filed on Jul. 28, 2004.

(51) Int. Cl.
*A61B 17/072* (2006.01)
*A61B 17/00* (2006.01)

(52) U.S. Cl. ............................... 227/180.1; 227/175.1; 606/219

(58) Field of Classification Search ............. 227/175.1, 227/176.1, 178.1, 180.1, 182.1, 19; 606/139, 606/219, 142
See application file for complete search history.

(56) References Cited

U.S. PATENT DOCUMENTS

| 5,465,895 | A |   | 11/1995 | Knodel et al. |
|---|---|---|---|---|
| 5,673,840 | A |   | 10/1997 | Schulze et al. |
| 5,829,662 | A | * | 11/1998 | Allen et al. ............... 227/177.1 |
| 5,901,895 | A | * | 5/1999 | Heaton et al. ........... 227/176.1 |
| 6,586,859 | B2 | * | 7/2003 | Kornbluh et al. ........... 310/309 |
| 6,667,825 | B2 |   | 12/2003 | Lu et al. |
| 2004/0232196 | A1 |   | 11/2004 | Shelton et al. |
| 2004/0232197 | A1 |   | 11/2004 | Shelton et al. |
| 2005/0006429 | A1 |   | 1/2005 | Wales et al. |
| 2005/0085693 | A1 | * | 4/2005 | Belson et al. ................ 600/146 |

* cited by examiner

*Primary Examiner*—Stephen F. Gerrity
*Assistant Examiner*—Paul Durand
(74) *Attorney, Agent, or Firm*—Dean L. Garner

(57) ABSTRACT

A surgical stapling instrument particularly suited to endoscopic use articulates an end effector (e.g., stapling and severing) that is actuated by a firing bar. An articulation mechanism in an elongate shaft incorporates electrically actuated polymer (EAP) actuators that laterally support the firing bar so that the firing bar is sufficiently constrained to avoid a blow-out, yet is guided without excessive friction and binding. Thereby, effective, consistent firing is accomplished without an undue increase in firing force required when the end effector is articulated.

17 Claims, 38 Drawing Sheets

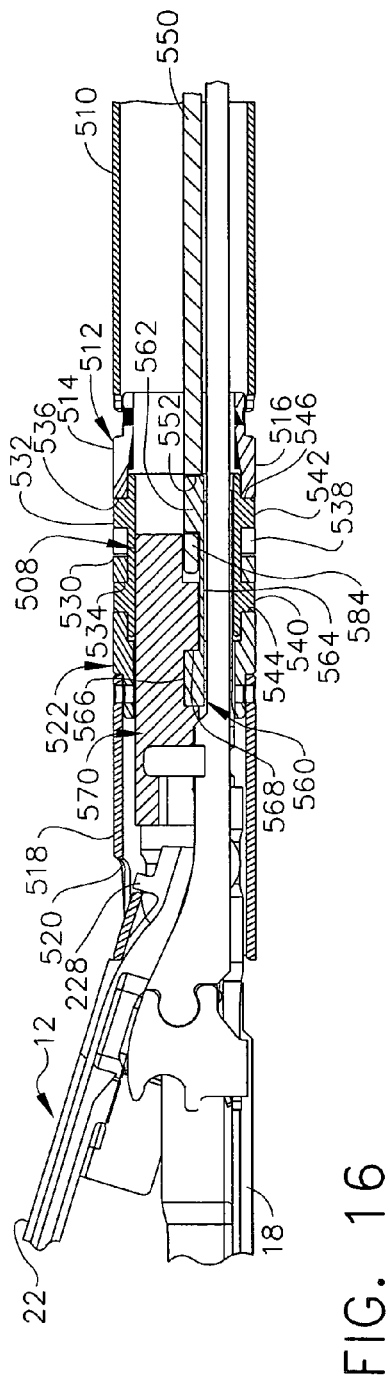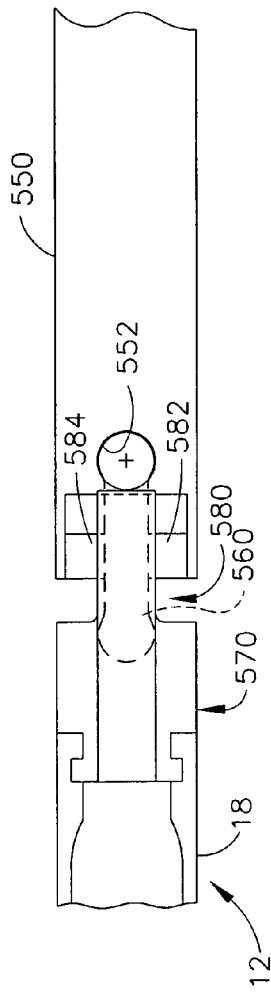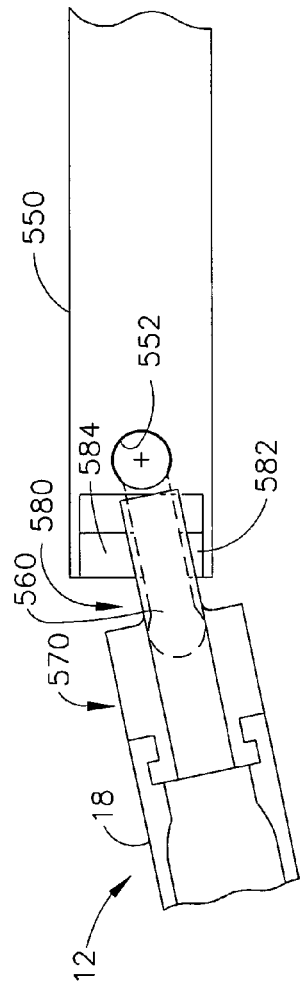
FIG. 16
FIG. 17
FIG. 18

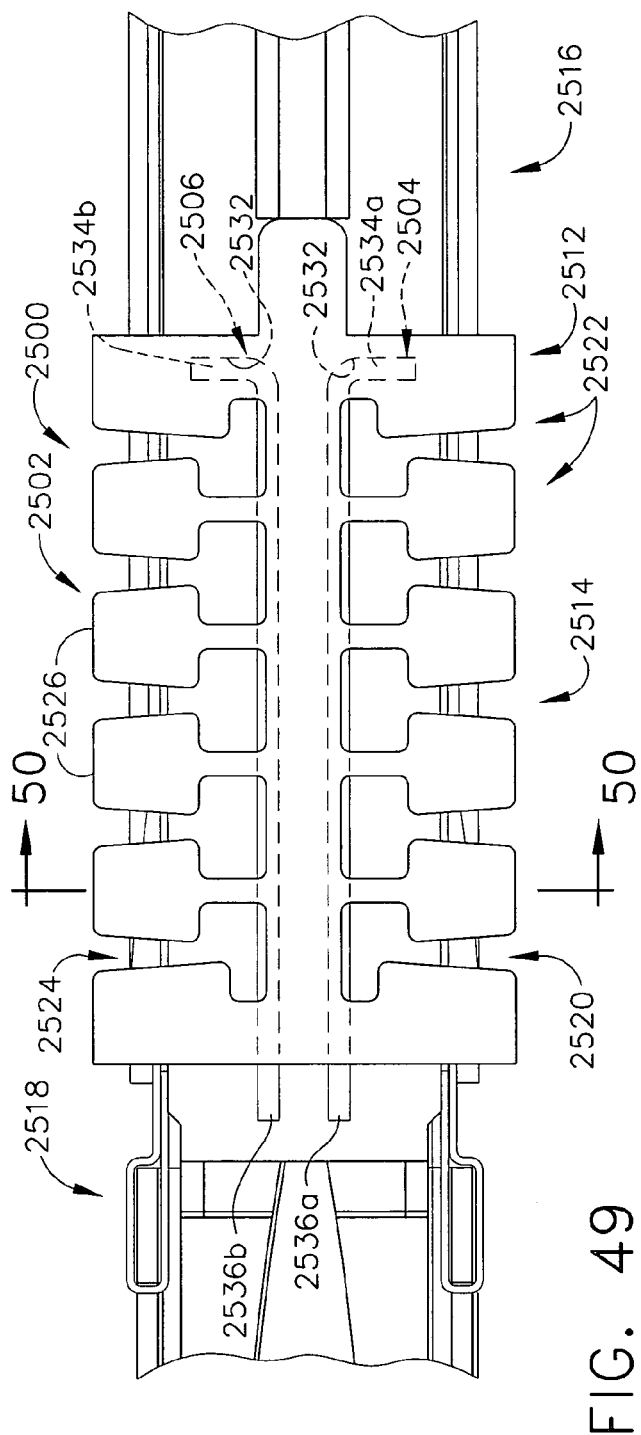
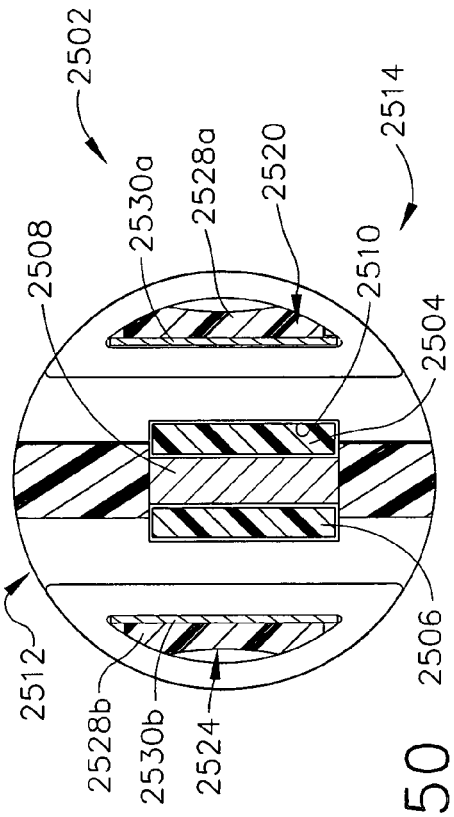
FIG. 49
FIG. 50

SURGICAL STAPLING INSTRUMENT INCORPORATING AN ELECTROACTIVE POLYMER ACTUATED FIRING BAR TRACK THROUGH AN ARTICULATION JOINT

CROSS REFERENCE TO RELATED APPLICATIONS

This application claims the benefit of U.S. Provisional Application Ser. No. 60/591,694, entitled "SURGICAL INSTRUMENT INCORPORATING AN ELECTRICALLY ACTUATED ARTICULATION MECHANISM" to Shelton IV, filed 28 Jul. 2004.

This application is a continuation-in-part of U.S. patent application Ser. No. 10/615,971, entitled "SURGICAL STAPLING INSTRUMENT HAVING ARTICULATION JOINT SUPPORT PLATES FOR SUPPORTING A FIRING BAR" to Wales, et al., filed 9 Jul. 2003 now U.S. Pat. No. 6,964,363, which is hereby incorporated by reference in its entirety.

FIELD OF THE INVENTION

The present invention relates in general to surgical instruments that are suitable for endoscopically inserting an end effector (e.g., endocutter, grasper, cutter, staplers, clip applier, access device, drug/gene therapy delivery device, and an energy device using ultrasound, RF, laser, etc.) to a surgical site, and more particularly to such surgical instruments with an articulating shaft.

BACKGROUND OF THE INVENTION

Endoscopic surgical instruments are often preferred over traditional open surgical devices since a smaller incision tends to reduce the post-operative recovery time and complications. Consequently, significant development has gone into a range of endoscopic surgical instruments that are suitable for precise placement of a distal end effector at a desired surgical site through a cannula of a trocar. These distal end effectors engage the tissue in a number of ways to achieve a diagnostic or therapeutic effect (e.g., endocutter, grasper, cutter, staplers, clip applier, access device, drug/gene therapy delivery device, and energy device using ultrasound, RF, laser, etc.).

Positioning the end effector is constrained by the trocar. Generally these endoscopic surgical instruments include a long shaft between the end effector and a handle portion manipulated by the clinician. This long shaft enables insertion to a desired depth and rotation about the longitudinal axis of the shaft, thereby positioning the end effector to a degree. With judicious placement of the trocar and use of graspers, for instance, through another trocar, often this amount of positioning is sufficient. Surgical stapling and severing instruments, such as described in U.S. Pat. No. 5,465,895, are an example of an endoscopic surgical instrument that successfully positions an end effector by insertion and rotation.

More recently, U.S. pat. Ser. No. 10/443,617, "SURGICAL STAPLING INSTRUMENT INCORPORATING AN E-BEAM FIRING MECHANISM" to Shelton et al., filed on 20 May 2003, which is hereby incorporated by reference in its entirety, describes an improved "E-beam" firing bar for severing tissue and actuating staples. Some of the additional advantages include affirmatively spacing the jaws of the end effector, or more specifically a staple applying assembly, even if slightly too much or too little tissue is clamped for optimal staple formation. Moreover, the E-beam firing bar engages the end effector and staple cartridge in a way that enables several beneficial lockouts to be incorporated.

Depending upon the nature of the operation, it may be desirable to further adjust the positioning of the end effector of an endoscopic surgical instrument. In particular, it is often desirable to orient the end effector at an axis transverse to the longitudinal axis of the shaft of the instrument. The transverse movement of the end effector relative to the instrument shaft is conventionally refeffed to as "articulation". This is typically accomplished by a pivot (or articulation) joint being placed in the extended shaft just proximal to the staple applying assembly. This allows the surgeon to articulate the staple applying assembly remotely to either side for better surgical placement of the staple lines and easier tissue manipulation and orientation. This articulated positioning permits the clinician to more easily engage tissue in some instances, such as behind an organ. In addition, articulated positioning advantageously allows an endoscope to be positioned behind the end effector without being blocked by the instrument shaft.

Approaches to articulating a surgical stapling and severing instrument tend to be complicated by integrating control of the articulation along with the control of closing the end effector to clamp tissue and fire the end effector (i.e., stapling and severing) within the small diameter constraints of an endoscopic instrument. Generally, the three control motions are all transferred through the shaft as longitudinal translations. For instance, U.S. Pat. No. 5,673,840 discloses an accordion-like articulation mechanism ("flex-neck") that is articulated by selectively drawing back one of two connecting rods through the implement shaft, each rod offset respectively on opposite sides of the shaft centerline. The connecting rods ratchet through a series of discrete positions.

In U.S. patent application Ser. No. 10/615,971, support plates are described that guide a firing bar through a pivoting articulation joint. Resilient or spring features at one or both ends advantageously compensate for the change in radial distance between the inner and outer support plates, thus maintaining a spacing therebetween to avoid binding. Thus, blowouts of the firing bar are avoided without introducing performance degradation, such as increasing the force required to actuate the firing mechanism.

While these generally-known approaches successfully support the firing bar through an articulation joint for a surgical stapling and severing instrument, it is desirable to further enhance their performance.

Consequently, a significant need exists for an improved articulating surgical instrument that supports a firing bar through an articulation joint.

BRIEF SUMMARY OF THE INVENTION

The invention overcomes the above-noted and other deficiencies of the prior art by providing a surgical instrument with an articulating shaft attached between a handle and an end effector. A pair of electroactive polymer (EAP) support members are disposed in an articulation joint of the shaft and are responsive to an electrical signal passed through the shaft. Each member is aligned with and laterally offset from the longitudinal axis of the articulation joint. Activating a selective EAP support member effects a longitudinal dimensional change to assist articulation.

In one aspect of the invention, a surgical instrument includes an end effector that is actuated by a firing bar that translates within the elongate shaft. The EAP support resides on each lateral side of the firing bar as it transitions through an articulation joint. By changing dimensionally the change in radius of rotation for the EAP support member on the inside of the articulation bend as compared to the EAP support member on the outside, spacing is preserved to effectively guide the firing bar without binding.

In another aspect of the invention, an articulating shaft of a surgical instrument is supported in articulating by having a pair of laterally offset, longitudinally aligned EAP support members that have one end longitudinally constrained and the other end slidingly received. The EAP support members are configured to bend when activated to assist in articulating.

In another aspect of the invention, an articulating shaft of a surgical instrument is supported in articulating by having a pair of laterally offset, longitudinally aligned EAP support members that have both ends longitudinally constrained respectively in the proximal and distal ends of the articulation joint. The EAP support members are confirmed to change in longitudinal length when activated to assist in articulation.

These and other objects and advantages of the present invention shall be made apparent from the accompanying drawings and the description thereof.

BRIEF DESCRIPTION OF THE FIGURES

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 16 is a right side view in elevation of the alternative EAP actuated articulation joint taken in cross section along lines 16—16 of FIG. 14 with firing components included.

FIG. 17 is a top view of the alternative EAP actuated articulation joint in an unarticulated condition taken in cross section along lines 17—17 of FIG. 14.

FIG. 18 is a top view of the alternative EAP actuated articulation joint in a leftward articulated condition taken in cross section along lines 17—17 of FIG. 14.

FIG. 49 is a top view of a flexible articulation joint incorporating EAP support plates of FIG. 45 or 46.

FIG. 50 is a front view in elevation of the flexible articulation joint of FIG. 49 taken through lines 49—49.

DETAILED DESCRIPTION OF THE INVENTION

Overview of Articulating Shaft.

Figure 1:
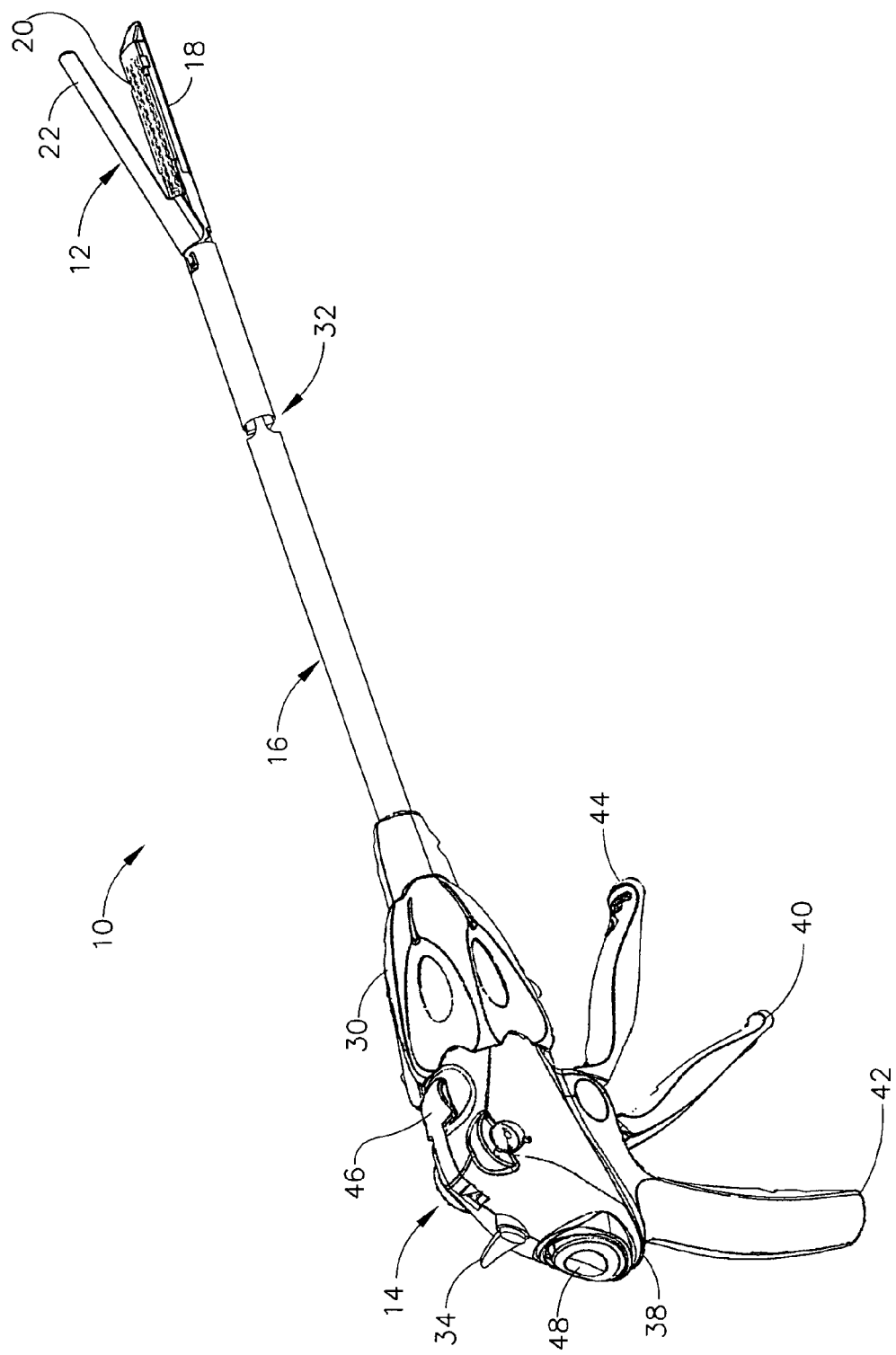
FIG. 1 is a rear perspective view of an endoscopic surgical stapling instrument for surgical stapling and severing in an open, unarticulated state.

In FIG. 1, a surgical instrument, depicted as a surgical severing and stapling instrument 10, has at its distal end an end effector of a staple applying assembly 12, spaced apart from a handle 14 by an elongate shaft 16. The staple applying assembly 12 includes a staple channel 18 for receiving a replaceable staple cartridge 20. Pivotally attached to the staple channel 18 is an anvil 22 that clamps tissue against the staple cartridge 20 for stapling and severing. When the staple applying assembly 12 is closed, its cross sectional area, as well as the elongate shaft 16, are suitable for insertion through a small surgical opening, such as through a cannula of a trocar (not shown).

Correct placement and orientation of the staple applying assembly 12 is facilitated by controls on the handle 14. In particular, a rotation knob 30 causes rotation of the shaft 16 about its longitudinal axis, and hence rotation of the staple applying assembly 12. Additional positioning is enabled at an articulation joint 32 in the shaft 16 that pivots the staple applying assembly 12 in an arc from the longitudinal axis of the shaft 16, thereby allowing placement behind an organ or allowing other instruments such as an endoscope (not shown) to be oriented behind the staple applying assembly 12. This articulation is advantageously effected by an articulation control switch 34 on the handle 14 that transmits an electrical signal to the articulation joint 32 to an Electroactive Polymer (EAP) actuator 36, powered by an EAP controller and power supply 38 contained within the handle 14.

Once positioned with tissue in the staple applying assembly 12, a surgeon closes the anvil 22 by drawing a closure trigger 40 proximally toward a pistol grip 42. Once clamped thus, the surgeon may grasp a more distally presented firing trigger 44, drawing it back to effect firing of the staple applying assembly 12, which in some applications is achieved in one single firing stroke and in other applications by multiple firing strokes. Firing accomplishes simultaneously stapling of at least two rows of staples while severing the tissue therebetween.

Retraction of the firing components may be automatically initiated upon full travel. Alternatively, a retraction lever 46 may be drawn aft to effect retraction. With the firing components retracted, the staple applying assembly 12 may be unclamped and opened by the surgeon slightly drawing the closure trigger 40 aft toward the pistol grip 42 and depressing a closure release button 48 and then releasing the closure trigger 40, thereby releasing the two stapled ends of severed tissue from the staple applying assembly 12.

It should be appreciated that herein spatial terms such as vertical, horizontal, etc. are given with reference to the figures assuming that the longitudinal axis of the surgical instrument 10 is horizontal with the anvil 22 of the staple applying assembly 12 aligned vertically on top and the triggers 40, 44 aligned vertically on the bottom of the handle 14. However, in actual practice the surgical instrument 10 may be oriented at various angles and as such these spatial terms are used relative to the surgical instrument 10 itself. Further, proximal is used to denote a perspective of a clinician who is behind the handle 14 who places the end effector 12 distal, away from himself.

Handle.

In FIG. 1, the staple applying assembly 12 accomplishes the functions of clamping onto tissue, driving staples and severing tissue by two distinct motions transferred longitudinally down the shaft 16 over a shaft frame (not shown in FIG. 1 but described below regarding FIG. 7). This shaft frame assembly is proximally attached to the handle 14 and coupled for rotation with the rotation knob 30. An illustrative multi-stroke handle 14 for the surgical stapling and severing instrument 10 of FIG. 1 is described in greater detail in the co-pending and co-owned U.S. patent applications entitled "SURGICAL STAPLING INSTRUMENT INCORPORATING A MULTISTROKE FIRING POSITION INDICATOR AND RETRACTION MECHANISM" to Swayze and Shelton, Ser. No. 10/674,026, and entitled "SURGICAL STAPLING INSTRUMENT INCORPORATING A MULTI-STROKE FIRING MECHANISM WITH AUTOMATIC END OF FIRING TRAVEL RETRACTION", Ser. No. 11/052,387, filed on Feb. 7, 2005 to Kevin R. Doll, Jeffrey S. Swayze, Frederick E. Shelton IV, Douglas B. Hoffman, and Michael E. Setser, the disclosures of which are hereby incorporated by reference in their entirety, with additional features and variations as described herein.

While a multi-stroke handle 14 advantageously supports applications with high firing forces over a long distance, applications consistent with the present invention may incorporate a single firing stroke, such as described in co-pending and commonly owned U.S. patent application "SURGICAL STAPLING INSTRUMENT HAVING SEPARATE DISTINCT CLOSING AND FIRING SYSTEMS" to Frederick E. Shelton IV, Michael E. Setser, and Brian J. Hemmelgam, Ser. No. 10/441,632, the disclosure of which is hereby incorporated by reference in its entirety.

Electroactive Polymers.

Electroactive polymers (EAPs) are a set of conductive doped polymers that change shape when an electrical voltage is applied. In essence, the conductive polymer is paired to some form of ionic fluid or gel and electrodes. Flow of the ions from the fluid/gel into or out of the conductive polymer is induced by the voltage potential applied and this flow induces the shape change of the polymer. The voltage potential ranges from 1V to 4 kV depending on the polymer and ionic fluid used. Some of the EAPs contract when voltage is applied and some expand. The EAPs may be paired to mechanical means such as springs or flexible plates to change the effect that is caused when the voltage is applied.

There are two basic types of electroactive polymers and multiple configurations of each type. The two basic types are a fiber bundle and a laminate version. The fiber bundle consists of fibers around 30–50 microns. These fibers may be woven into a bundle much like textiles and are often called EAP yarn because of this. This type of EAP contracts when voltage is applied. The electrodes are usually a central wire core and a conductive outer sheath, which also serves to contain the ionic fluid that surrounds the fiber bundles. An example of a commercially available fiber EAP material is manufactured by Santa Fe Science and Technology, and is sold as PANION™ fiber and is described in U.S. Pat. No. 6,667,825, which is hereby incorporated by reference in its entirety.

The other type is a laminate structure, which consists of a layer of EAP polymer, a layer of ionic gel and two flexible plates that are attached to either side of the laminate. When a voltage is applied, the square laminate plate expands in one direction and contracts in the perpendicular direction. Artificial Muscle Inc., a division of SRI Laboratories, manufactures an example of a commercially available laminate (plate) EAP material. Plate EAP material is also available from EAMEX of Japan and is referred to as thin film EAP.

It should be noted that EAPs do not change volume when energized; they merely expand or contract in one direction while doing the opposite in the transverse direction. The laminate version may be used in its basic form by placing one side against a rigid structure and using the other much like a piston. It may also be adhered to either side of a flexible plate. When one side of the flexible plate EAP is energized, it expands, flexing the plate in the opposite direction. This allows the plate to be flexed either direction depending on which side is energized.

An EAP actuator usually consists of numerous layers or fibers bundled together to work in cooperation. The mechanical configuration of the EAP determines the EAP actuator and its capabilities for motion. The EAP may be formed into long stands and wrapped around a single central electrode. A flexible exterior outer sleeve forms the other electrode for the actuator as well as contains the ionic fluid necessary for the function of the device. In this configuration when the electrical field is applied to the electrodes, the strands of EAP shorten. This configuration of the EAP actuator is called a fiber EAP actuator. Likewise, the laminate configuration may be placed in numerous layers on either side of a flexible plate or merely in layers on itself to increase its capabilities. Typical fiber structures have an effective strain of 2–4% where the typical laminate version achieves 20–30% utilizing much higher voltages.

Figure 2:
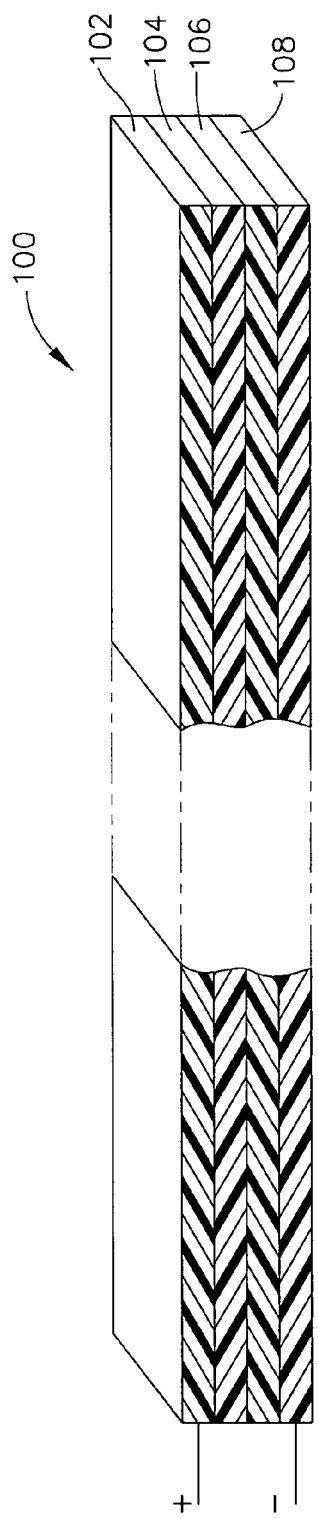
FIG. 2 is a perspective view of a laminate Electroactive Polymer (EAP) composite.
Figure 3:
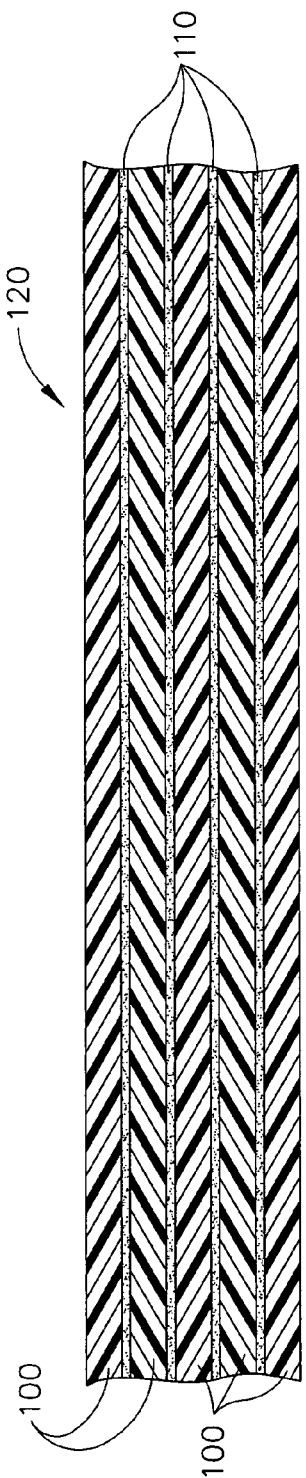
FIG. 3 is a perspective view of an EAP plate actuator formed from a stack formed from an adhesively affixed plurality of laminate EAP composites of FIG. 2.

In FIG. 2, a laminate EAP composite 100 is depicted as being formed from a positive plate electrode layer 1302 attached to an EAP layer 104, which in turn is attached to an ionic cell layer 106, which in turn is attached to a negative plate electrode layer 108. In FIG. 3, a plurality of five laminate EAP composites 100 are affixed in a stack by adhesive layers 110 therebetween to form an EAP plate actuator 120. It should be appreciated that opposing EAP actuators 120 may be formed that can selectively bend in either direction. For example, the laminate EAP composite 100 may be differentially activated such that layers on one side either expand or contract, depending on the configuration of the EAP, thus effecting bending relative to a nonactivated layer. As another example, a non-EAP substrate such as spring steel, resin or polymer is attached to the laminate EAP composite 100. Thus, a laminate EAP composite 100 configured to elongate would cause bending of the non-EAP substrate away from the laminate EAP composite 100. A laminate EAP composite 100 configured to contract would cause bending of the non-EAP substrate toward the laminate EAP composite. Having laminate EAP composite 100 on both sides of the non-EAP substrate may be used to differentially effect bending in either direction.

Figure 4:
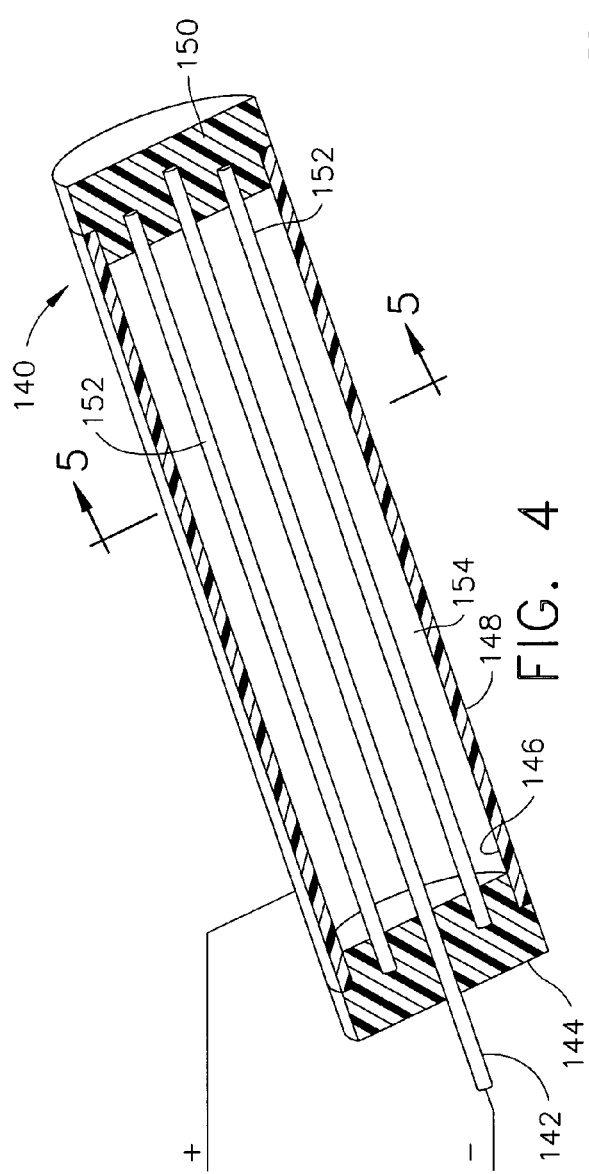
FIG. 4 is a perspective view of a cutaway along a longitudinal axis of a contracting EAP fiber actuator.
Figure 5:
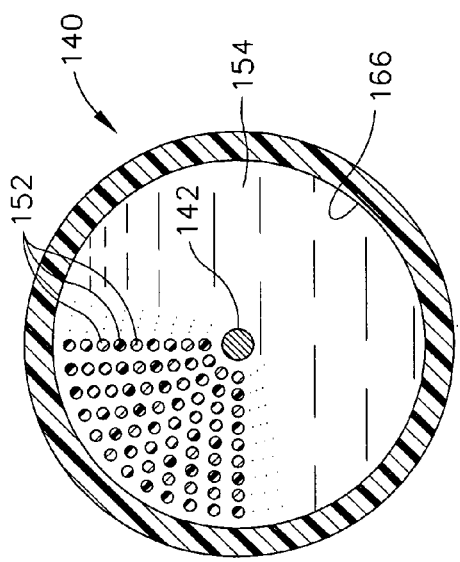
FIG. 5 is a front view in elevation taken in cross section along lines 5—5 of the contracting EAP fiber actuator of FIG. 4.

In FIGS. 4–5, a contracting EAP fiber actuator 140 includes a longitudinal platinum cathode wire 142 that passes through an insulative polymer proximal end cap 144 through an elongate cylindrical cavity 146 formed within a plastic cylinder wall 148 that is conductively doped to serve as a positive anode. A distal end of the platinum cathode wire 142 is embedded into an insulative polymer distal end cap 150. A plurality of contracting polymer fibers 152 are arranged parallel with and surrounding the cathode wire 142 and have their ends embedded into respective end caps 144, 150. The plastic cylinder wall 148 is peripherally attached around respective end caps 144, 150 to enclose the cylindrical cavity 146 to seal in ionic fluid or gel 154 that fills the space between contracting polymer fibers 152 and cathode wire 142. When a voltage is applied across the plastic cylinder wall (anode) 148 and cathode wire 142, ionic fluid enters the contracting polymer fibers 152, causing their outer diameter to swell with a corresponding contraction in length, thereby drawing the end caps 144, 150 toward one another.

EAP Actuated Articulation Joint.

In FIGS. 6–13, a surgical severing and stapling instrument 200 includes an EAP actuated articulation joint 202 that is formed in its elongate shaft 204 proximate to the end effector, which is illustrated by the surgical stapling and severing assembly 12 that advantageously responds to separate closure and firing motions that are transferred longitudinally by the elongate shaft 204. The EAP actuated articulation joint 202 advantageously adds the desirable clinical flexibility of articulating the staple applying assembly 12.

Figure 6:
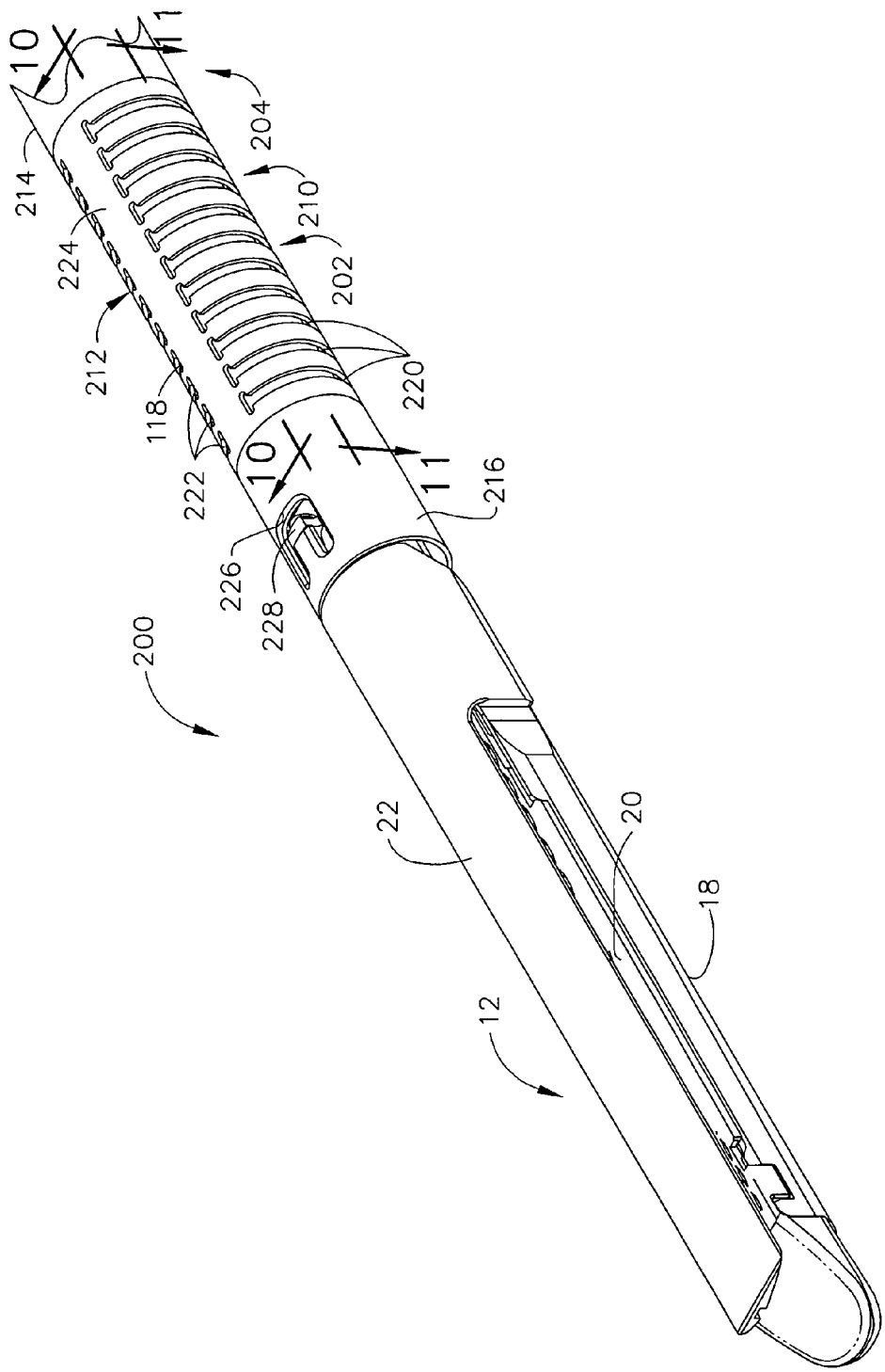
FIG. 6 is a front right perspective view of an EAP actuated articulation joint for the surgical instrument of FIG. 1 with a flexible closure sleeve assembly, a pivoting frame assembly and a closed staple applying assembly.
Figure 7:
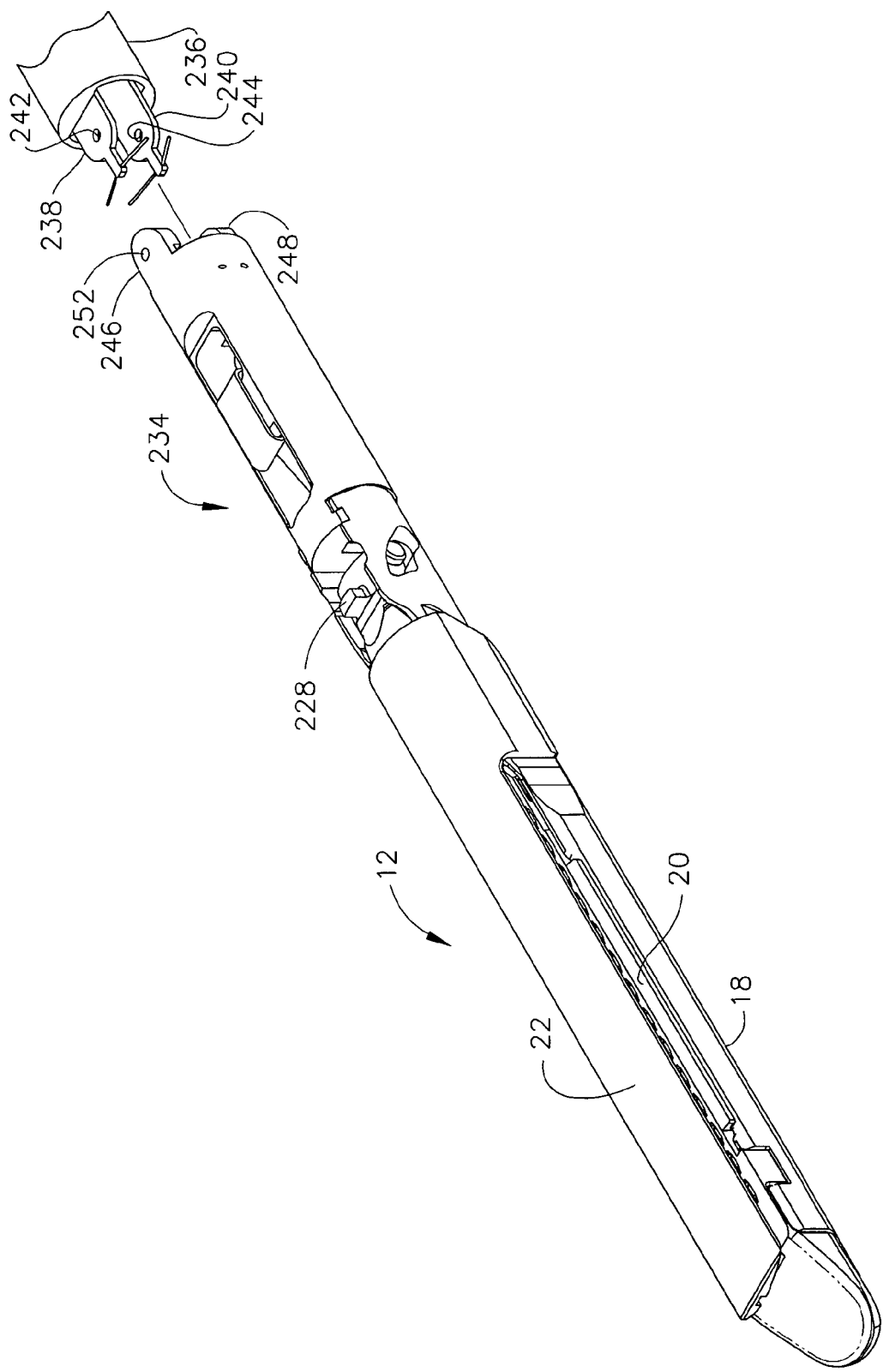
FIG. 7 is a front right perspective view of the EAP actuated articulation joint and closed staple applying assembly of FIG. 6 with a flexible closure sleeve assembly removed and a single pivot frame assembly partially exploded.
Figure 8:
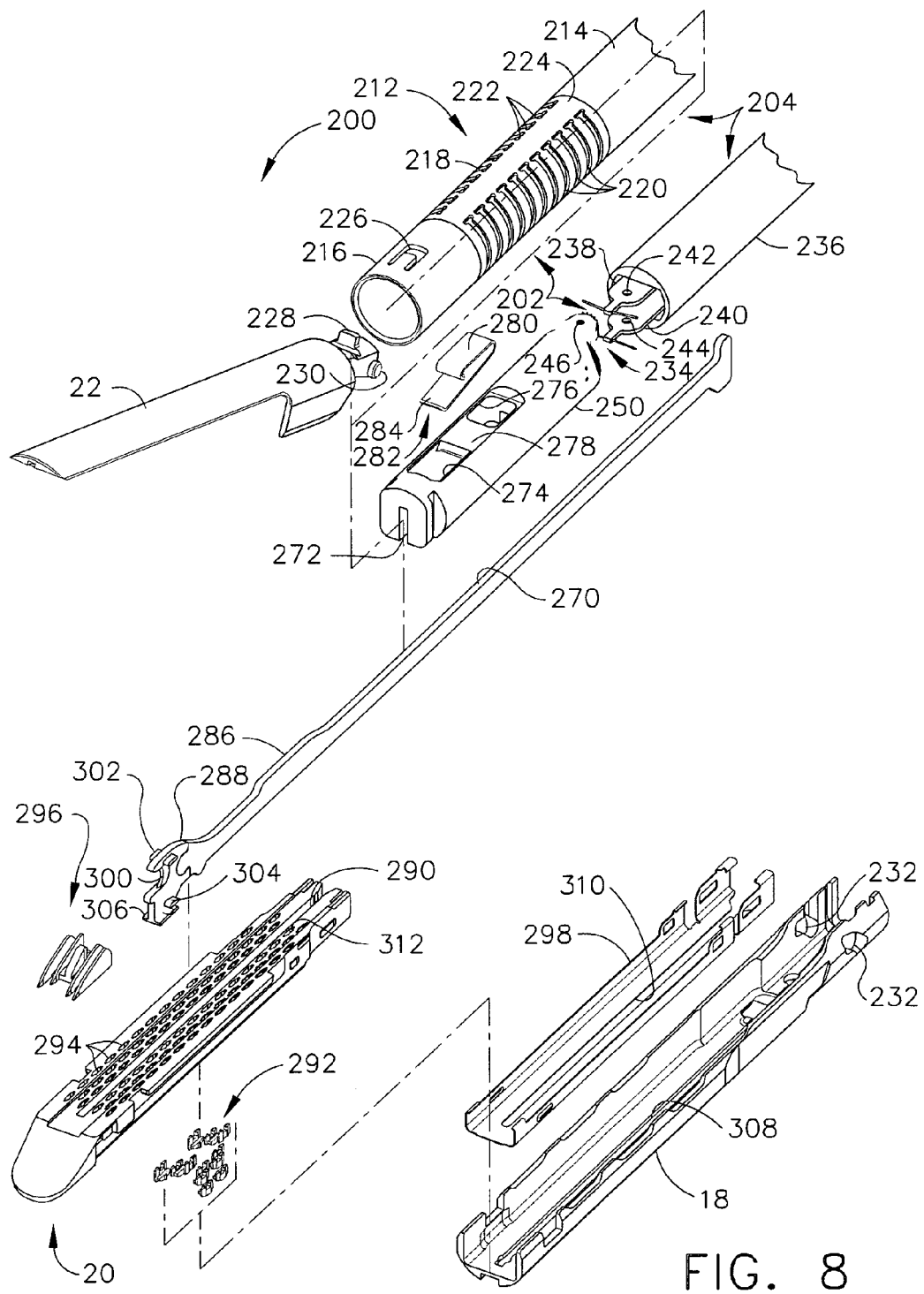
FIG. 8 is a front right exploded perspective view of the EAP actuated articulation joint and staple applying assembly of FIG. 6.

In the illustrative version of FIGS. 6–13, the EAP actuated articulation joint 202 is more particularly a flexible closure and pivoting frame articulation joint 210, which in FIG. 6 is shown to include a flexible closure sleeve assembly 212 having a proximal closure tube 214 and distal closure ring 216 connected by a flexible closure tube 218. Left and right longitudinal rows of vertical slits 220, 222 formed in the flexible closure tube 218 allow flexing to the right or to the left for articulation, yet an uninterrupted top longitudinal band 224 transfers a longitudinal closure motion, regardless of the amount of such flexing. It should be appreciated that an identical uninterrupted bottom longitudinal band runs along the bottom of the flexible closure tube 218 (not shown) and is opposite to and cooperates with the top longitudinal band 224 in transferring this motion. In particular, a top portion of the distal closure ring 216 includes a horseshoe aperture 226 that engages an anvil closure feature 228 of the anvil 22. In FIG. 7, the anvil 22 includes laterally projecting pivot pins 230 at its proximal end that pivotally engage pivot apertures 232 formed near the proximal end of the elongate channel 18 (FIGS. 7–8). The slightly more distal anvil closure feature 228 thus imparts a closing motion when the flexible closure sleeve assembly 212 moves distally and imparts an opening motion when moving proximally. The flexible closure tube 218 may bend along the length of the left and right longitudinal rows of vertical slits 220, 222, thus accommodating an encompassed single pivot frame assembly 234 of the flexible closure and pivoting frame articulation joint 210 when articulated.

Figure 9:
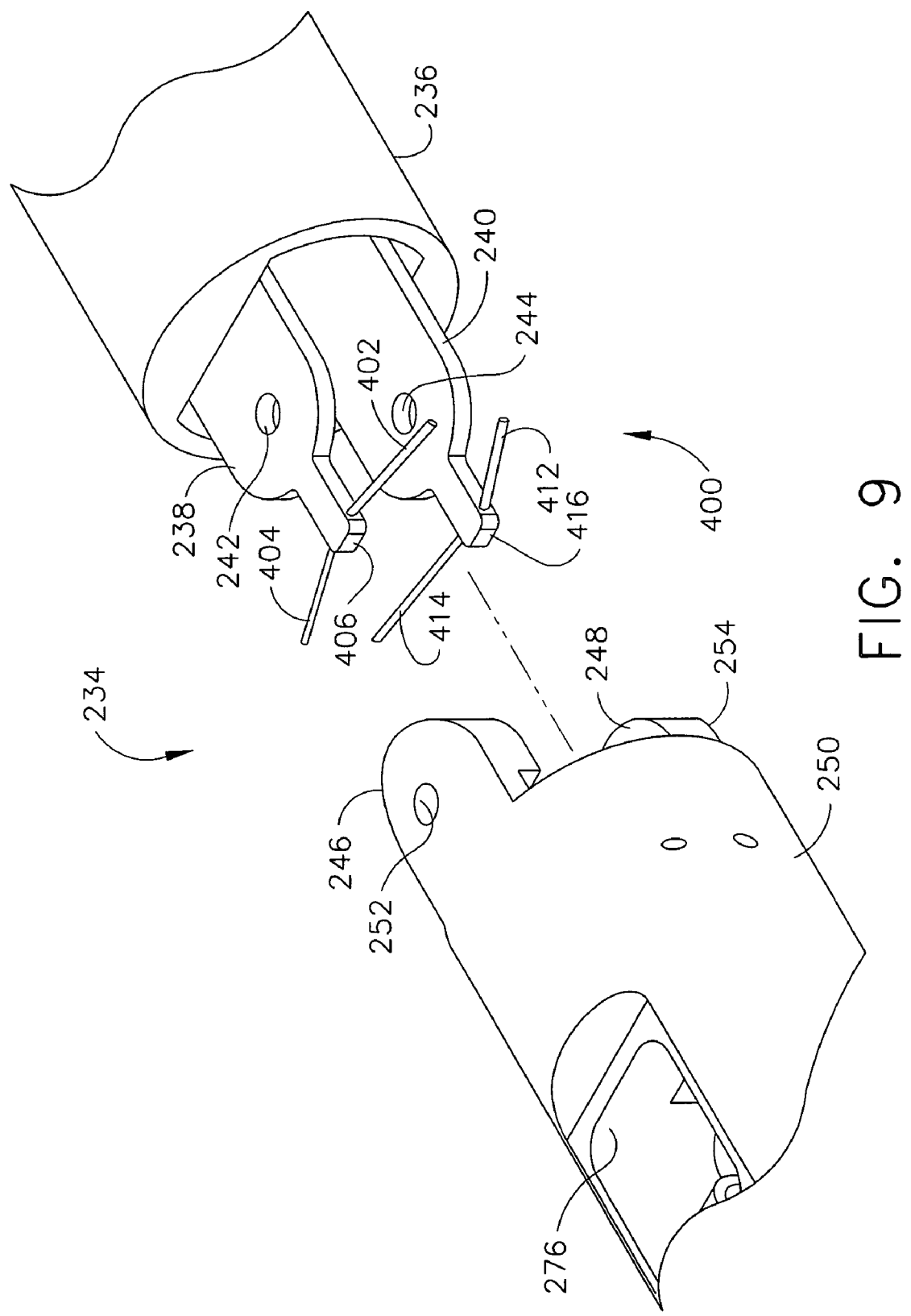
FIG. 9 is a detail view of the exploded single pivot frame assembly including EAP fiber actuators of FIG. 7.
Figure 10:
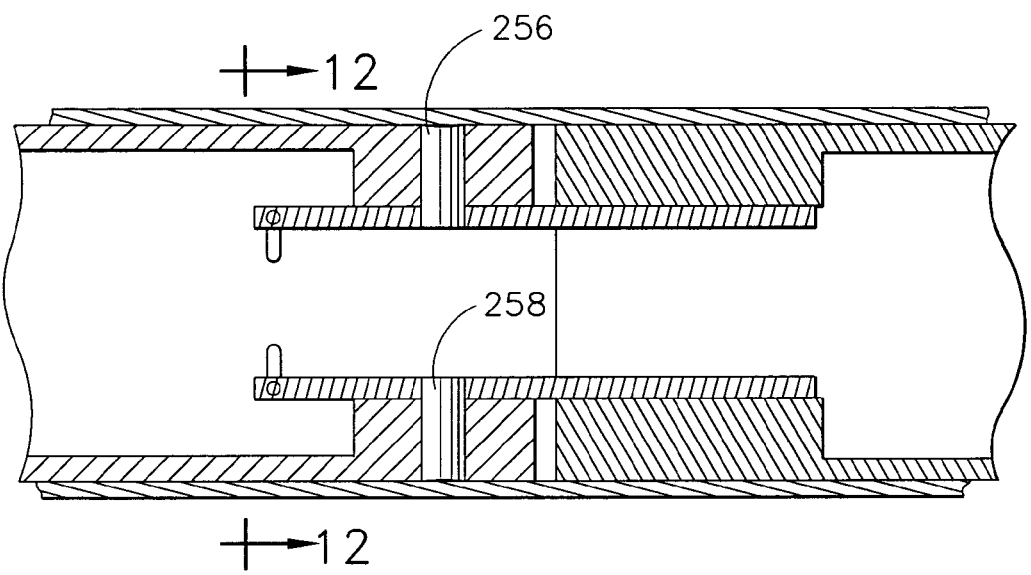
FIG. 10 is a right side view in elevation taken in cross section along lines 10—10 of FIG. 6 through a pivot axis of the EAP actuated articulation joint and looking right to see a pair of EAP fiber actuators.
Figure 11:
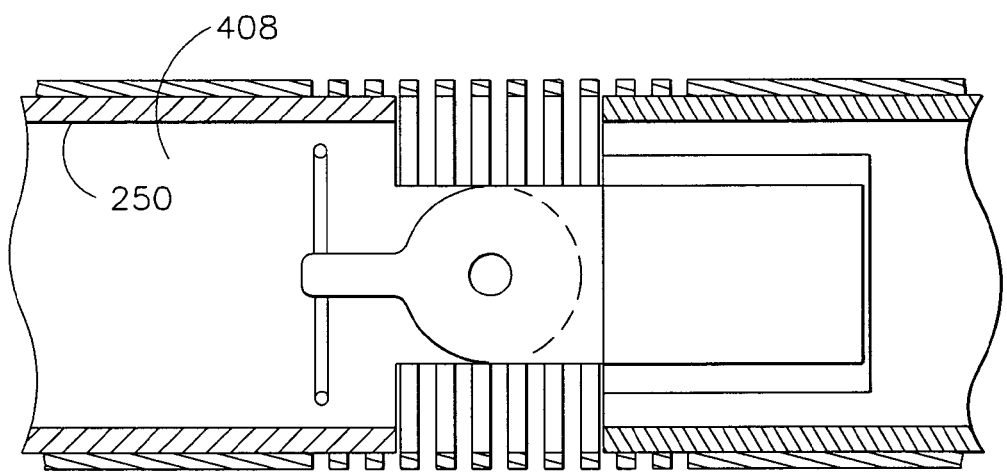
FIG. 11 is a top view taken in cross section along lines 11—11 of FIG. 11 through a longitudinal axis of the EAP actuated articulation joint looking down to see a lower moment arm and lower EAP fiber actuators.
Figure 12:
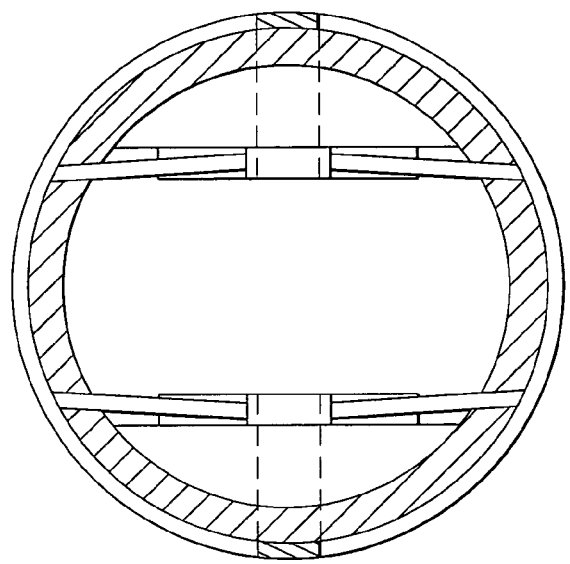
FIG. 12 is a front view in elevation taken in cross section along lines 12—12 of FIG. 10 along the lateral EAP fiber actuators.
Figure 13:
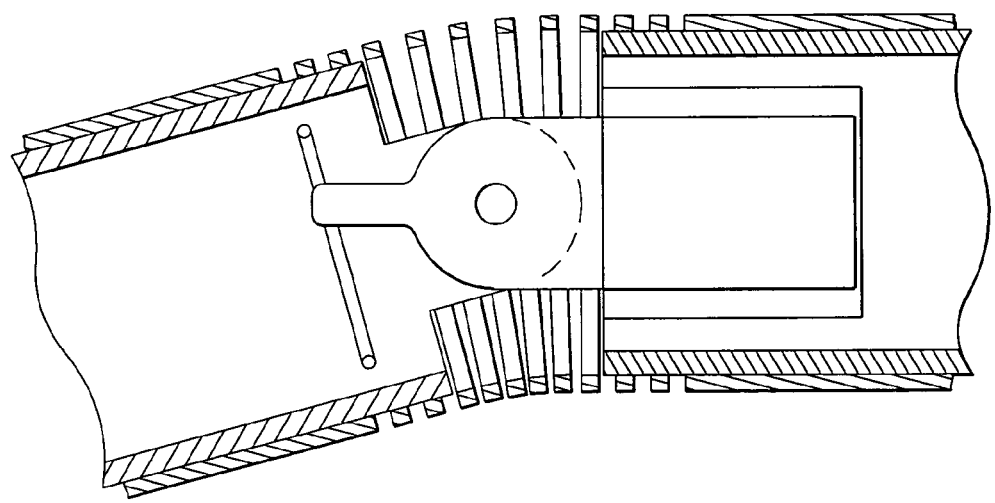
FIG. 13 is a top view of the EAP actuated articulation joint of FIG. 11 with the right upper and lower EAP fiber actuators contracted to articulate the staple applying assembly to the left.

With particular reference to FIGS. 7–9, the single pivot frame assembly 234 includes a proximal frame ground 236 with distally projecting top and bottom pivot tabs 238, 240, each having a respective top and bottom pivot pin hole 242, 244. Corresponding top and bottom pivot tangs 246, 248 projecting proximally from a distal frame ground 250, each tang 246, 248 with respective top and bottom pivot pin holes 252, 254, pivotally engage the proximal frame ground 236. In particular, the vertically aligned top pivot pin holes 242, 252 and bottom pivot pin holes 244, 254 are respectively engaged by top and bottom frame pivot pins 256, 258 (FIG. 10).

In FIG. 8, an implement portion 260 of the surgical instrument 200, formed by the elongate shaft 16 and staple applying assembly 12, further includes a firing bar 270 that longitudinally translates through the proximal frame ground 218, through the flexible closure and pivoting frame articulation joint 210, and through a firing slot 272 in the distal frame ground 250 into the staple applying assembly 12. Distal and proximal square apertures 274, 276 formed on top of the distal frame ground 250 define a clip bar 278 therebetween that receives a top arm 280 of a clip spring 282 whose lower, distally extended arm 284 asserts a downward pressure on a raised portion 286 along an upper portion of the firing bar 270 corresponding to the empty/missing cartridge lockout portion of firing travel.

With particular reference to FIG. 8, a distally projecting end of the firing bar 270 is attached to an E-beam 288 that assists in spacing the anvil 22 from the staple cartridge 20, severs tissue, and actuates the staple cartridge 20. The staple cartridge 20 includes a molded cartridge body 290 that holds a plurality of staples resting upon staple drivers 292 within respective upwardly open staple apertures 294. A wedge sled 296 is driven distally by the E-beam 28 21'8, sliding upon a cartridge tray 298 that holds together the various components of the replaceable staple cartridge 20. The wedge sled 296 upwardly cams the staple drivers 292 to force out the staples into deforming contact with the anvil 22 while a cutting surface 300 of the E-beam 288 severs clamped tissue. It should be appreciated that upper pins 302 of the E-beam 288 engage the anvil 22 during firing while middle pins 304 and a bottom foot 306 engage respective top and bottom surfaces of a longitudinal slot 308 formed in the elongate channel 18, with a corresponding longitudinal opening 310 in the cartridge tray 298 and a rearwardly open vertical slot 312 in the cartridge body 290. Thereafter, the firing bar 270 is retracted proximally, retracting as well the E-beam 288, allowing the anvil 22 to be opened to release the two stapled and severed tissue portions (not shown).

The staple applying assembly 12 is described in greater detail in co-pending and commonly-owned U.S. patent application Ser. No. 10/955,042, "ARTICULATING SURGICAL STAPLING INSTRUMENT INCORPORATING A TWO-PIECE E-BEAM FIRING MECHANISM" to Frederick E. Shelton IV, et al., filed 30 Sep. 2004, the disclosure of which is hereby incorporated by reference in its entirety.

With particular reference to FIGS. 9–13, an EAP actuator system 400 advantageously actuates the single pivot frame assembly 234 in response to an electrical articulation signal (not shown) received from the handle 14. In the illustrative version of FIGS. 7–13, top left and top right EAP fiber actuators 402, 404 attach horizontally to each lateral side of a top distally projecting moment arm 406 attached to the top pivot tab 238. The outer ends of the top left and top right EAP fiber actuators 402, 404 are attached to respective upper left and right lateral attachment points 406, 408 of an inner diameter 410 of the distal frame ground 250. Similarly, bottom left and bottom right EAP fiber actuators 412, 414 attach horizontally to each lateral side of a bottom distally projecting moment arm 416 attached to the top pivot tab 238. The outer ends of the bottom left and bottom right EAP fiber actuators 412, 414 are attached to respective lower left and right lateral attachment points 418, 420 of the inner diameter 410 of the distal frame ground 250. The attachments points 406, 408, 418, 420 are shown to pass through the distal frame ground 250 in FIG. 12 with the left attachment points 406, 418 visible on the exterior of the distal frame ground 250 in FIG. 9. Activating one pair of EAP actuators, such as in FIG. 13, and in particular reference to the upper and lower right EAP fiber actuators 404, 414, causes them to contract, drawing the upper and lower moment arms 406, 416 toward the right side of the distal frame ground 250, thereby stretching the upper and lower EAP fiber actuators 402, 412, collapsing the left longitudinal row of vertical slits 220, and expanding the right longitudinal row of vertical slits 222.

Figure 14:
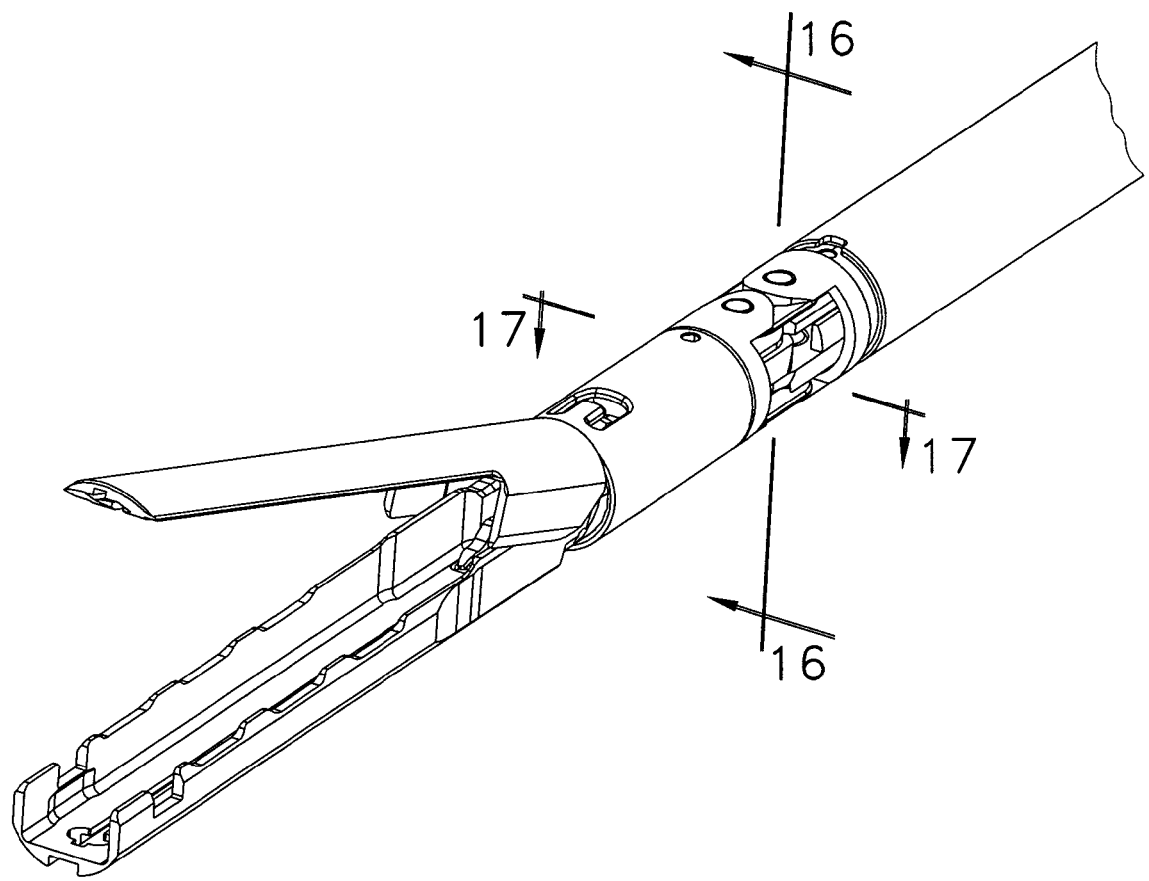
FIG. 14 is a front right perspective view of an additional alternative EAP actuated articulation joint that includes a double pivot closure sleeve assembly in a proximal position opening of the anvil of the end effector.

In FIGS. 14–18, a surgical severing and stapling instrument 500 includes an alternative EAP actuated articulation joint 502 that includes a double pivot closure sleeve assembly 504 (FIG. 14–15) and a single pivot frame assembly 506 (FIG. 15–18). In FIG. 14, the staple applying assembly 12 is depicted with the replaceable staple cartridge 20 removed and the anvil 22 open. Thus, the double pivot closure sleeve assembly 504 is at its proximal position with its distal pivoting axis aligned with a pivoting axis of the frame assembly 506. It should be appreciated that with the closure sleeve assembly 504 moved distally to close the anvil 22, a proximal pivot axis of the closure sleeve assembly 504 also pivots in order to translate over an articulated frame assembly 506.

Figure 15:
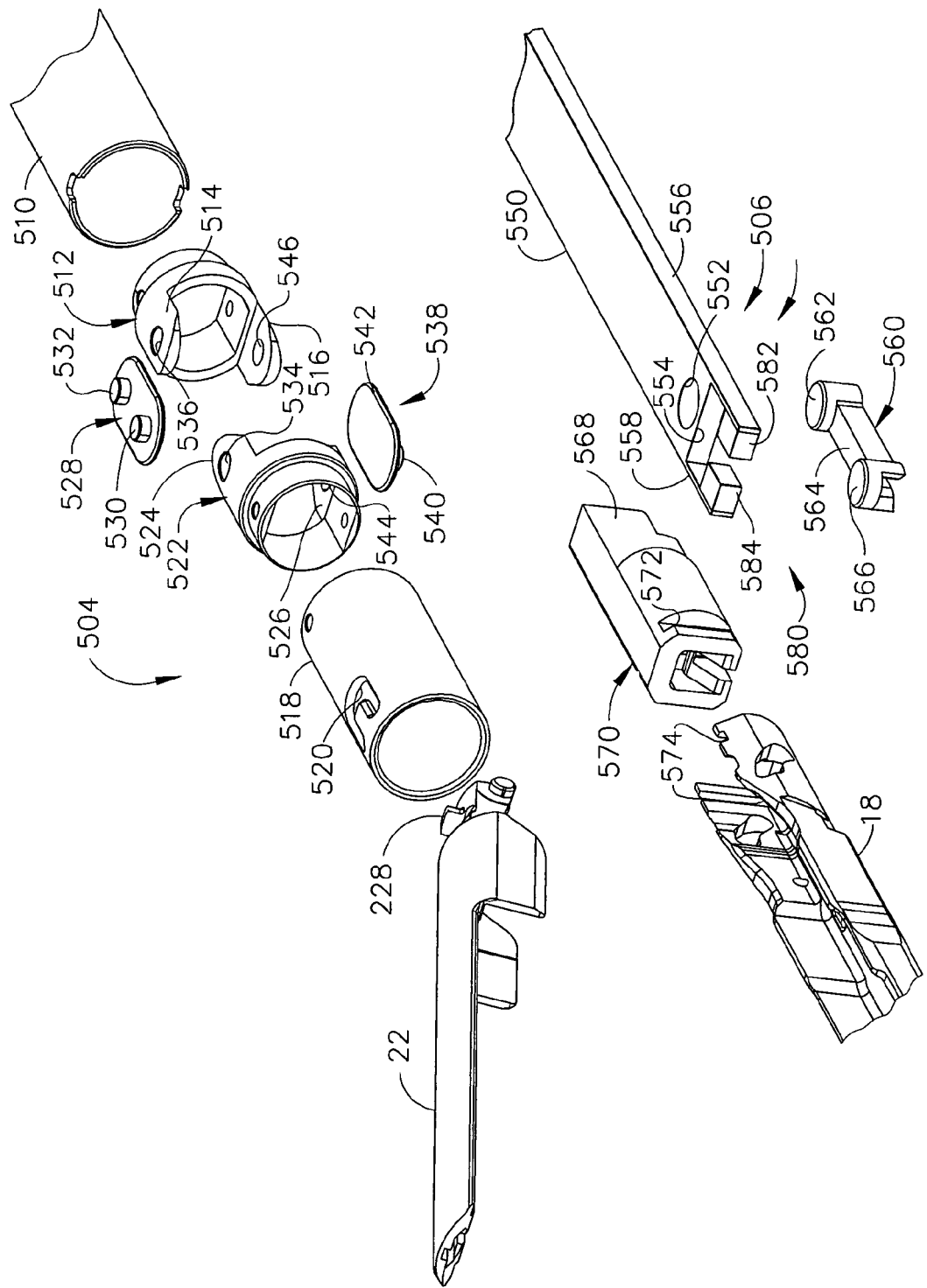
FIG. 15 is a front right exploded view of the additional alternative EAP actuated articulation joint of FIG. 14 including the double pivot closure sleeve assembly and a single pivot frame assembly.

With particular reference to FIG. 15, the double pivot closure sleeve assembly 504 includes a proximal closure tube 510 whose distal end is keyed to attach to a proximal closure ring 512 having upper and lower distally projecting tangs 514, 516. A distal closure tube 518, which includes a horseshoe aperture 520 to engage the anvil closure feature 228 on the anvil 22, is proximally pinned to a distal closure ring 522 having upper and lower proximally projecting tangs 524, 526. An upper double pivot link 528 includes upwardly projecting distal and proximal pivot pins 530, 532 that engage respectively an upper distal pin hole 534 in the upper proximally projecting tang 524 and an upper proximal pin hole 536 in the upper distally projecting tang 514. A lower double pivot link 538 includes downwardly projecting distal and proximal pivot pins 540, 542 that engage respectively a lower distal pin hole 544 in the lower proximally projecting tang 526 and a lower proximal pin hole 546 in the lower distally projecting tang 516.

With particular reference to FIGS. 15–18, the single pivot frame assembly 506 includes a proximal frame ground 550 whose distal end includes a pivot pin hole 552 centered and proximal to a distally open pivot recess 554 defined between left and right moment arms 556, 558. A dog bone link 560 includes a proximal pin 562 that upwardly engages the pivot pin hole 552 in the proximal frame ground 550 and a center bar 564 that pivots between the left and right moment arms 556, 558. A distal pin 566 of the dog bone link 560 is rigidly attached into a lower proximal bore 568 in a distal frame ground 570 having distal lateral guides 572 that engage proximal guides 574 in the elongate channel 18.

An EAP actuation system 580 includes left and right EAP stack actuators 582, 584 that selectively expand to assert an articulation force on the center bar 564 of the dog bone link 560, which passively compresses the other EAP stack actuator. In FIG. 18, the right EAP stack actuator 582 has expanded, pivoting the dog bone link 560, and thus the staple applying assembly 12, to the left and passively compressing the left EAP stack actuator 584.

Figure 19:
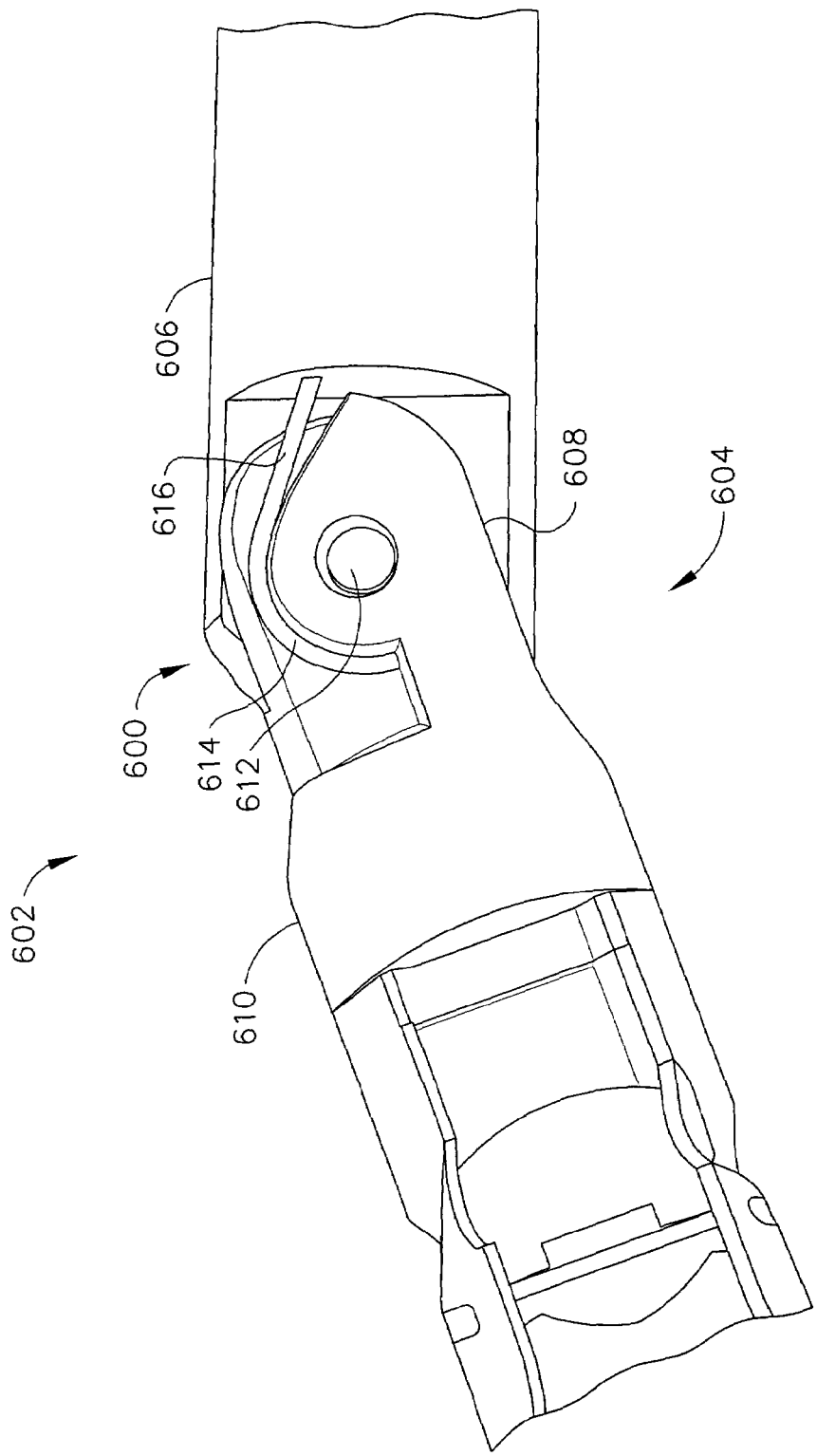
FIG. 19 is yet another alternative EAP actuated articulation joint in a slightly articulated condition with a contracting EAP fiber actuator positioned to straighten the joint.
Figures 20, 21:
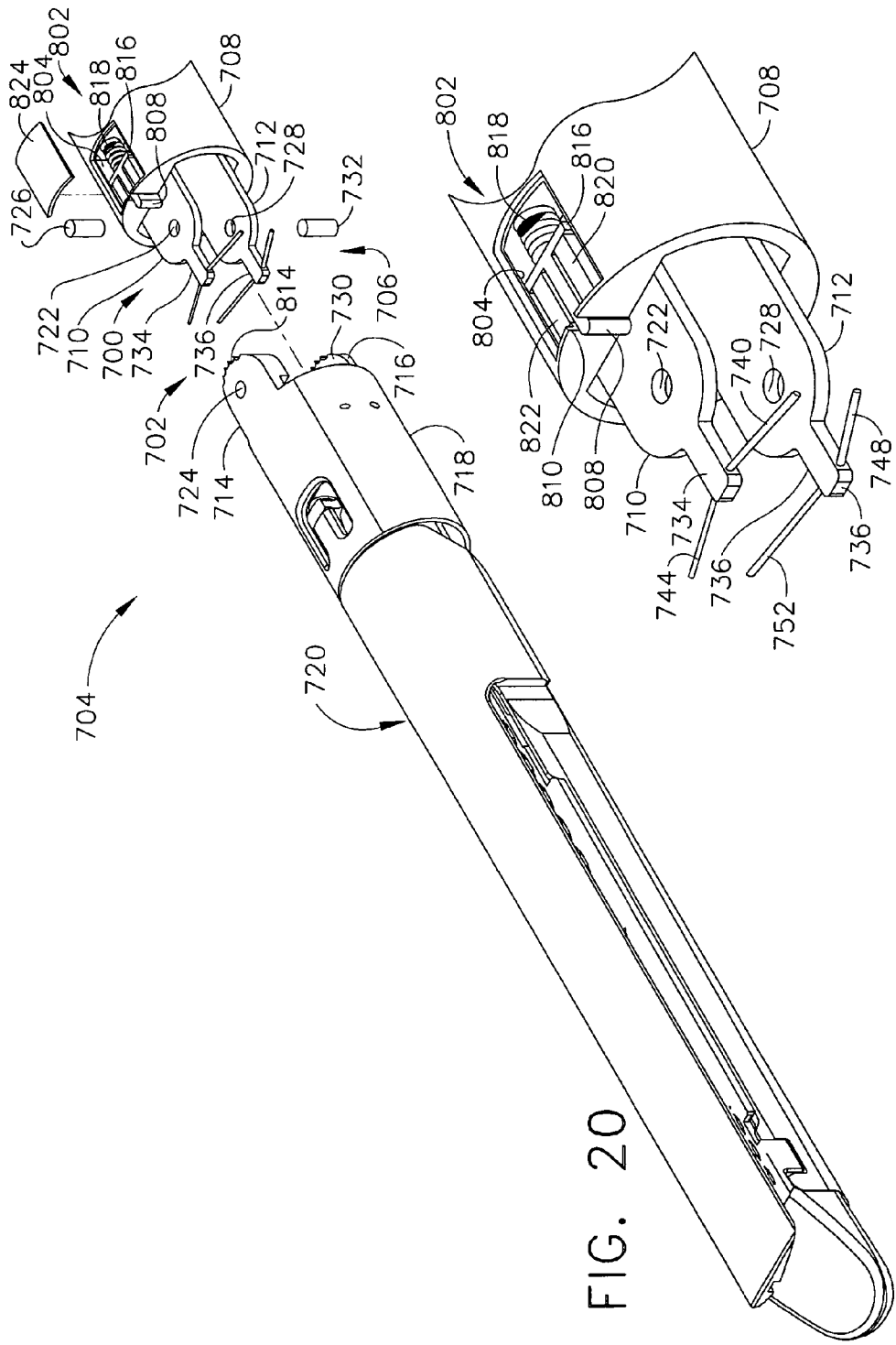
FIG. 20 is a right front perspective view of a partially exploded single pivot articulation joint that advantageously includes an EAP articulation locking mechanism that is biased to be normally locked.
FIG. 21 is a right front perspective view in detail of a proximal portion of the EAP articulation locking mechanism in a proximal frame ground of the single pivot articulation joint.
Figure 22:
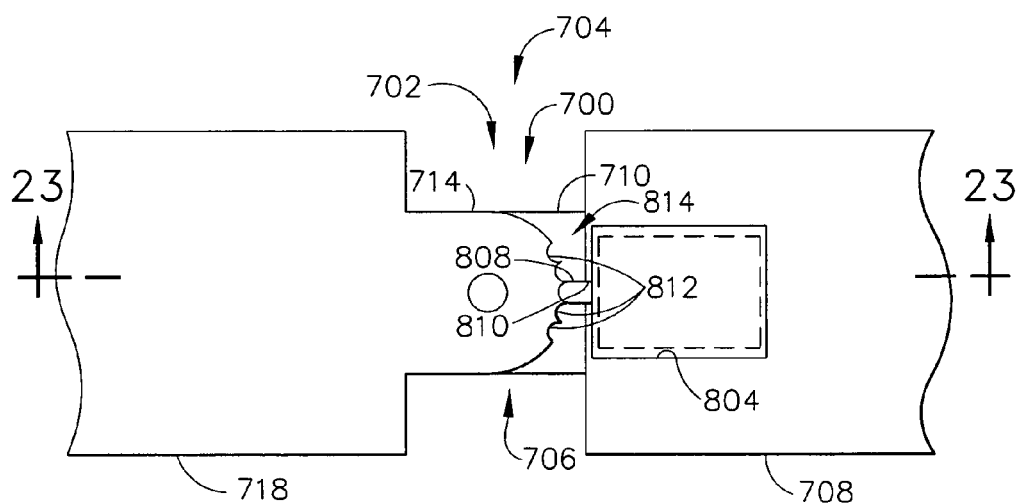
FIG. 22 is a top view of the single pivot articulation joint of FIG. 20.

In FIG. 19, yet another alternative EAP actuated articulation joint 600 for a surgical instrument 602 includes a single pivoting frame assembly 604 wherein a proximal frame ground 606 is engaged to a distally projecting tang 608 from a distal frame ground 610 at a pivot pin 612. The distally projecting tang 608 is recessed on a right lateral side to define a half teardrop shaped pulley 614 on the right side of the pivot pin 612. Attached to a distal point of the half teardrop shaped pulley 614 is a distal end of a contracting EAP fiber actuator 616 that follows the contour thereof and passes into the proximal frame ground 606. The contracting EAP fiber actuator 616 may be sufficiently long so that, for even a small percentage contraction in a length, a significant rotation may be achieved. It should be appreciated that a counter rotating mechanism may be incorporated on a left side of the depicted tang 608 on a similar but reversed mechanism formed on the other side of the EAP articulation joint 600.

Articulation Locking Mechanism for Pivoting Articulation Mechanism.

In FIGS. 20–27, an EAP actuated articulation lock 700 is incorporated into a pivoting articulation joint 702 for a surgical instrument 704. For clarity, a single pivoting frame assembly 706 is depicted with a proximal frame ground 708 having distally extended upper and lower pivot tabs 710, 712 that are pivotally engaged to proximally directed upper and lower tangs 714, 716 of a distal frame ground 718 that is attached to an end effector 720. An upper inner hole 722 in the upper pivot tab 710 is aligned under an upper outer hole 724 in the upper tang 714, which are pivotally pinned together by upper pivot pin 726. A lower inner hole 728 in the lower pivot tab 712 is aligned above a lower outer hole 730 in the lower tang 716. Holes 728,712 are pivotally pinned together by a lower pivot pin 732. Upper and lower moment arms 734, 736 extend distally respectively from the upper and lower pivot tabs 710, 712. The upper moment arm 734 may be urged to the left toward an upper left attachment point 738 formed in the distal frame ground 718 by a generally horizontal upper left EAP fiber actuator 740. The upper moment arm 734 may be urged to the right toward an upper right attachment point 742 formed in the distal frame ground 718 by a generally horizontal upper right EAP fiber actuator 744. The lower moment arm 736 may be urged to the left toward a lower left attachment point 746 formed in the distal frame ground 718 by a generally horizontal lower left EAP fiber actuator 748. The lower moment arm 736 may be urged to the right toward a lower right attachment point 750 formed in the distal frame ground 718 by a generally horizontal lower right EAP fiber actuator 752.

Closure of the anvil 22 may occur by action of a closure mechanism that is not shown, such as an EAP actuator that acts upon the anvil pivot. Alternatively, a firing motion may first close the anvil prior to further motion effecting stapling and severing. As a further alternative, a closure sleeve assembly or other longitudinally coupled mechanism (not shown) may impart a closing motion to the anvil 22.

An upper EAP actuated articulation locking mechanism 800 advantageously unlocks the pivoting articulation joint 702 to allow articulating movement. The EAP actuated articulation locking mechanism 800 then relaxes to a locked state, providing a stable locked position that does not require power dissipation, and thus component heating, between changes in an amount of articulation. An upper locking bolt assembly 802 is shown in a rectangular upper lock recess 804 formed in the proximal frame ground 708 proximal to and vertically farther from the longitudinal centerline than the upper pivoting tab 710. A locking bolt 806 extends a locking tip 808 out of a distal slot 810, formed in the upper lock recess 804, into engagement in a nearest tooth root 812 of a gear segment 814 formed about a proximal surface about the upper pivot tang 714 of the distal frame ground 718. The locking bolt 806 proximally terminates in cross plate 816 that slides longitudinally in the rectangular upper lock recess 804 between the urging of a proximally positioned compression spring 818 and upper left and right EAP stack actuator 820, 822 that may be activated to expand longitudinally, compressing the compression spring 818 as the lock bolt 806 is moved proximally, thereby disengaging the locking tip 808 from the gear segment 814, allowing the pivoting articulation joint 702 to be repositioned. An upper lock cover 824 closes the upper lock recess 804.

Figure 23:
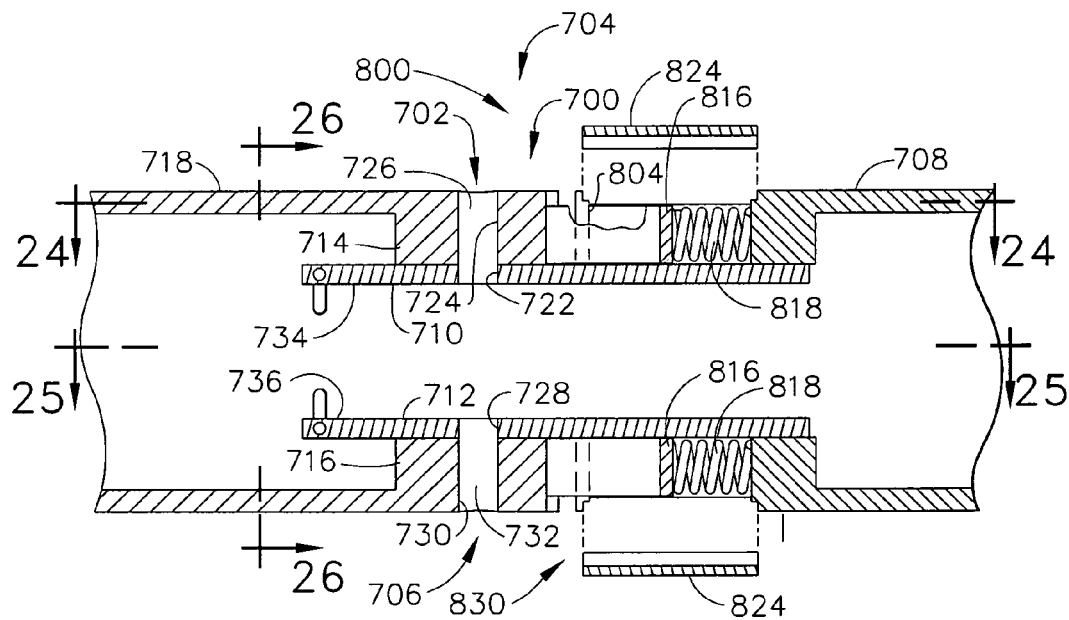
FIG. 23 is a right side view in elevation of the single pivot articulation joint of FIG. 22 taken in cross section along a longitudinal centerline of lines 23—23.
Figure 24:
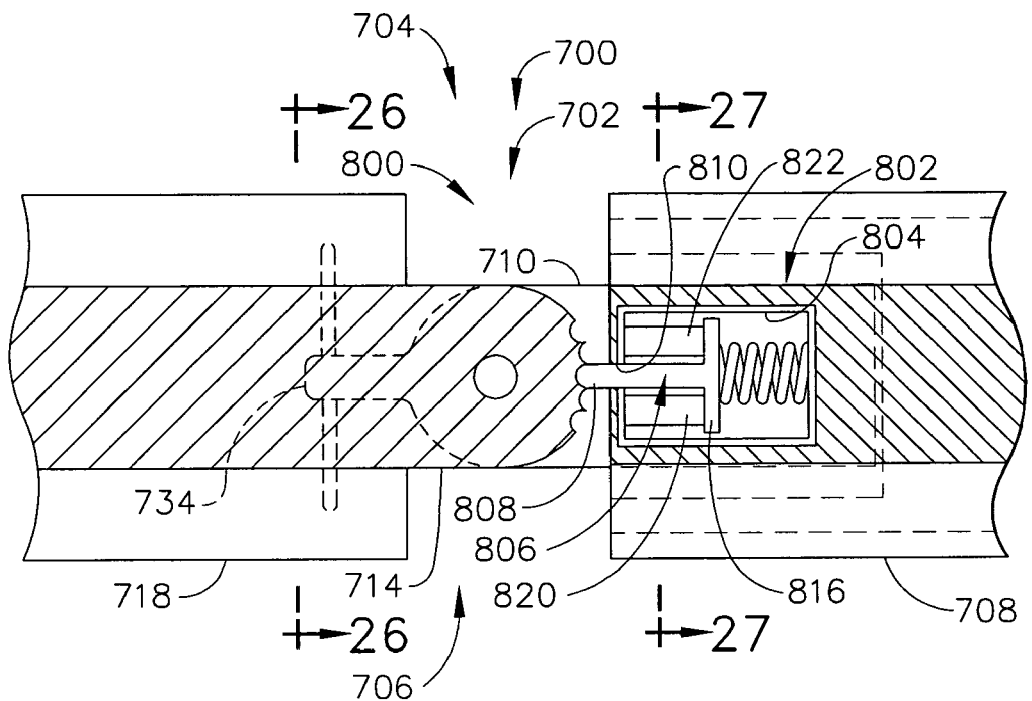
FIG. 24 is a top view of the single pivot articulation joint of FIG. 23 taken in cross section along lines 24—24 to show a gear segment on an upper pivot tang locked by the EAP articulation locking mechanism in an unarticulated condition.
Figure 25:
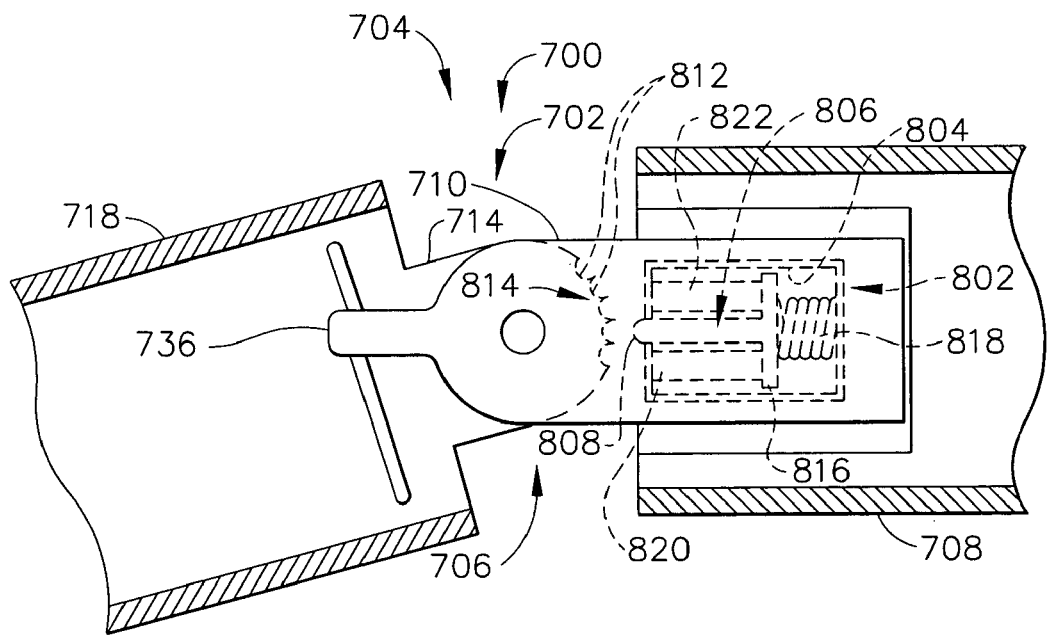
FIG. 25 is a top view of the single pivot articulation joint of FIG. 23 taken in cross section along a centerline of lines 24—24 looking down upon a lower pivot tab of a proximal frame ground that is partially articulating an end effector to the left while the EAP articulation locking mechanism is activated to an unlocked condition.
Figure 26:
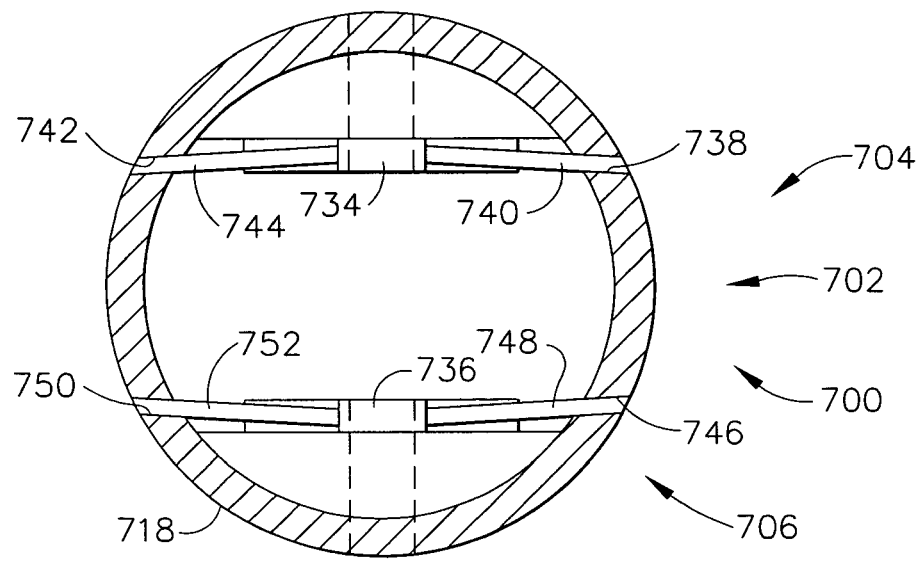
FIG. 26 is a front view in elevation of a distal frame ground of the single pivot articulation mechanism of FIG. 24 taken in cross section along lines 26—26 depicting attachment of EAP fiber actuators that articulate the joint.
Figure 27:
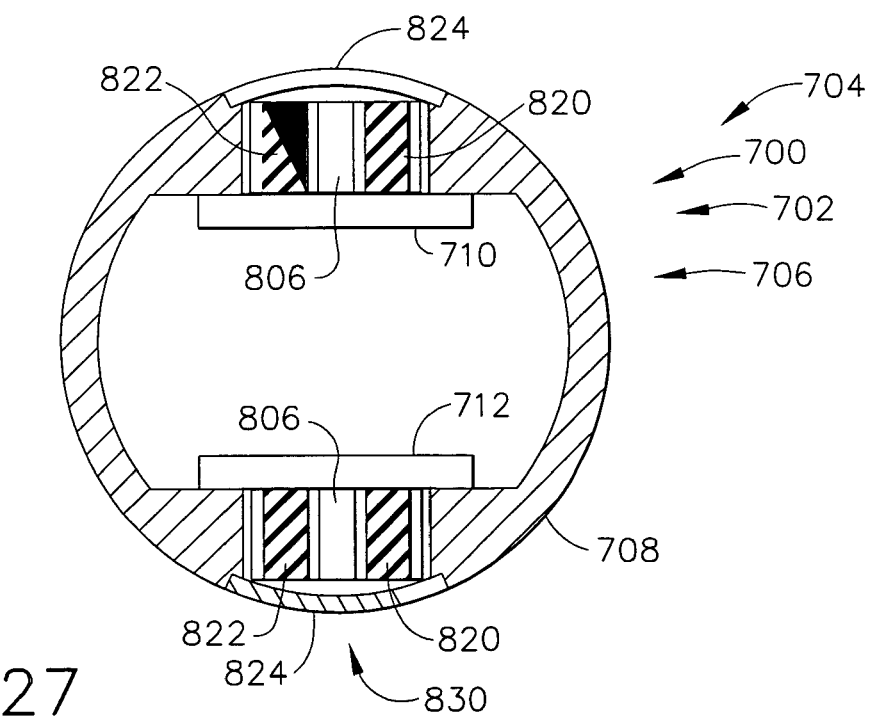
FIG. 27 is a front view in elevation of the proximal frame ground of the single pivot articulation joint of FIG. 24 taken in cross section along lines 27—27 to expose EAP stack actuators and locking pins of the EAP actuated locking mechanisms.

For additional locking support, in FIG. 23, a lower EAP actuated articulation locking mechanism 830, that is identical to the upper locking mechanism 800, acts on the opposite site against lower pivot tang 716. It should further be appreciated that a similar locking mechanism may be incorporated into a distal portion of an elongate shaft rather than a proximal end. Further, a double pivoting coupling may include a lock at each pivot.

In use, an unarticulated end effector 720 and pivoting articulation joint 702 (FIGS. 20–24) are inserted to a surgical site. With EAP locking mechanisms 800, 830 typically deenergized, the locking tip 808 attached to the proximal frame ground 708 engages the gear segment 814 of the distal frame ground 718, locking the single pivot frame assembly 706. When desired, EAP stack actuators 820, 822 are energized to longitudinally lengthen, unlocking the EAP articulation locking mechanisms 800, 830. While unlocked, the articulation joint 702 may be articulated, such as by contracting upper and lower right EAP fiber actuators 744, 752 to pivot the end effector 720 to the left (FIG. 25), presenting a different tooth root 812 to the locking tip 808 so that when deenergized the EAP articulation locking mechanism 800 will lock to the articulation condition of the surgical instrument 704.

Figure 28:
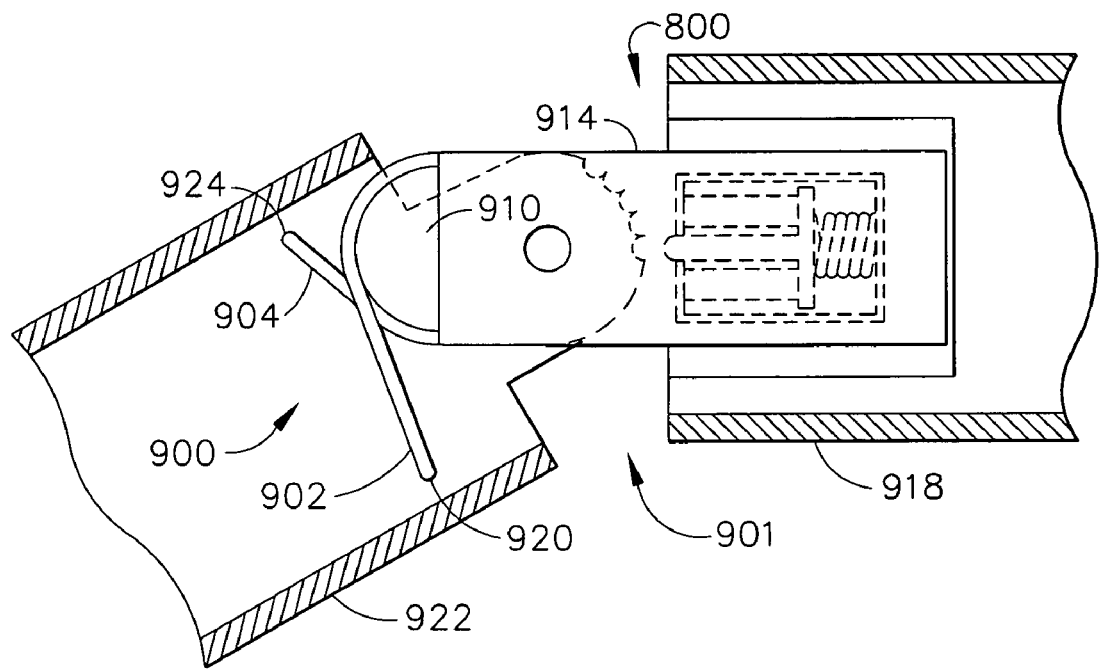
FIG. 28 is a top view taken in cross section along an interface between an upper pivot tang of a distal frame ground and an upper pivot tab of a proximal frame ground of a single pivot articulation joint with lengthened EAP fiber actuators acting upon rounded moment arms in combination with the EAP articulation locking mechanism.
Figure 29:
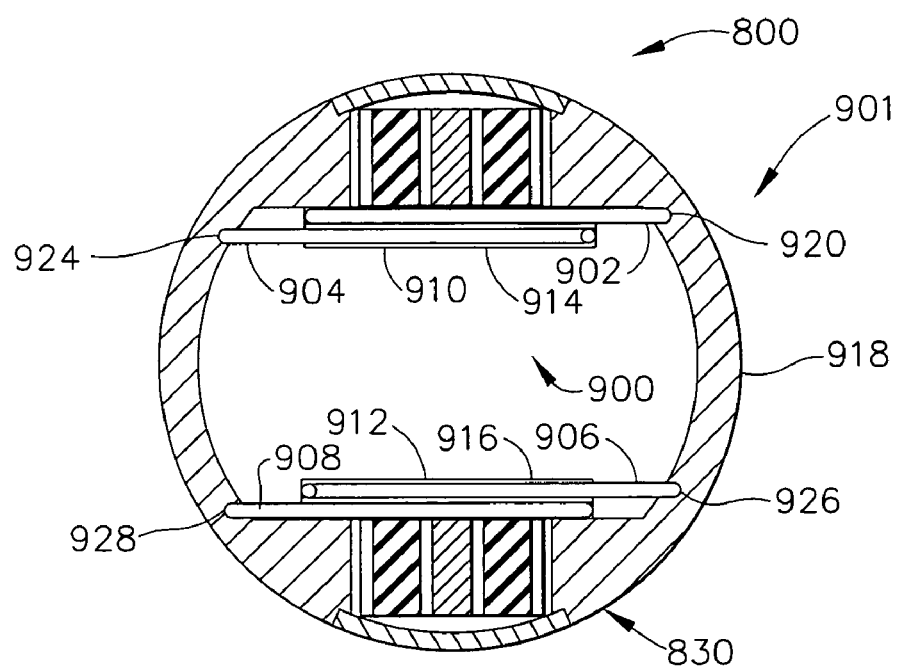
FIG. 29 is a front view in elevation taken generally in cross section through the proximal frame ground and EAP articulation locking mechanism but also showing more distally viewed moment arms and lengthened EAP fiber actuators connected thereto.

In FIGS. 28–29, an alternative EAP articulation system 900 for a single pivot articulation joint 901 is depicted for use in conjunction with the EAP articulation locking mechanism 800 previously described. Upper and lower pairs of left and right EAP fiber actuators 902, 904, 906, 908 are lengthened by incorporating upper and lower rounded moment arms 910, 912 distally respectively on upper and lower pivot tabs 914, 916 of a proximal frame ground 918. An upper left attachment point 920 in a distal frame ground 922 is slightly higher than an upper right attachment point 924. A lower left attachment point 926 is also slightly higher than a lower right attachment point 928, corresponding to the upper and lower left EAP fiber actuators 902, 906 wrapping respectively around a higher portion of the corresponding upper and lower rounded moment arms 910, 912 than the upper and lower right EAP fiber actuators 904, 908 (FIG. 29). Thereby, the lengthened EAP fiber actuators 902–908 in combination with the length and contour of the moment arms 910, 912 may be selected for a desired performance characteristic.

In FIGS. 30–33, an additional alternative EAP articulation system 1000 for a single pivot articulation joint 1001 is depicted for use in conjunction with the EAP articulation locking mechanism 800 previously described. Instead of EAP fiber actuators that effect articulation, upper and lower pairs of left and right EAP stack actuators 1002, 1004, 1006, 1008 respectively oppose and laterally move upper and lower longitudinal tracks 1010, 1012. A distally projecting upper moment arm 1014 attaches to an upper pivot tab 1016 of a proximal frame ground 1018. An upper inwardly directed tip pin 1020 at a distal end of the upper moment arm 1014 longitudinally slidingly engages the upper longitudinal track 1010, and thus responds to the differential contraction and expansion of the upper left and right EAP stack actuators 1002, 1004 that are laterally constrained by a distal frame ground 1022. A distally projecting lower moment arm 1024 attaches to an upper pivot tab 1026 of the proximal frame ground 1018. A lower inwardly directed tip pin 1030 at a distal end of the upper moment arm 1024 longitudinally slidingly engages the lower longitudinal track 1012, and thus responds to the differential contraction and expansion of the lower left and right EAP stack actuators 1006, 1008 that are laterally constrained by the distal frame ground 1022.

Figure 30:
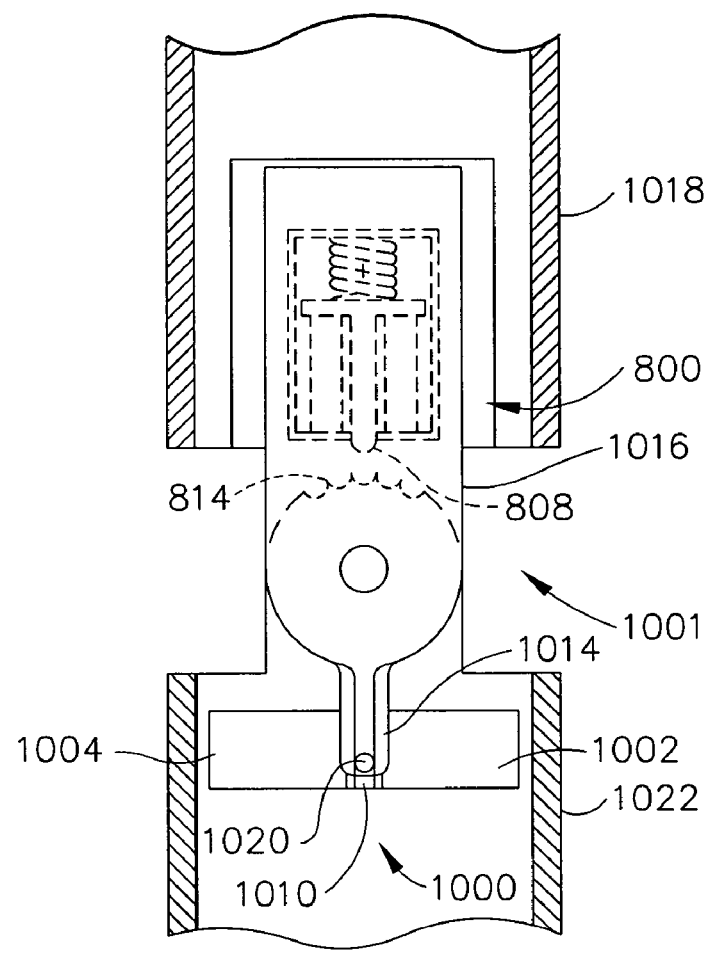
FIG. 30 is a top view of a single pivot articulation joint taken in cross section along a top surface of an upper pivot tab of a proximal frame ground to illustrate expansive EAP stack actuators employed against a moment arm distally attached to the upper pivot tab to effect articulation used in conjunction with the normally locked EAP articulation locking mechanism activated in preparation for articulation.
Figure 31:
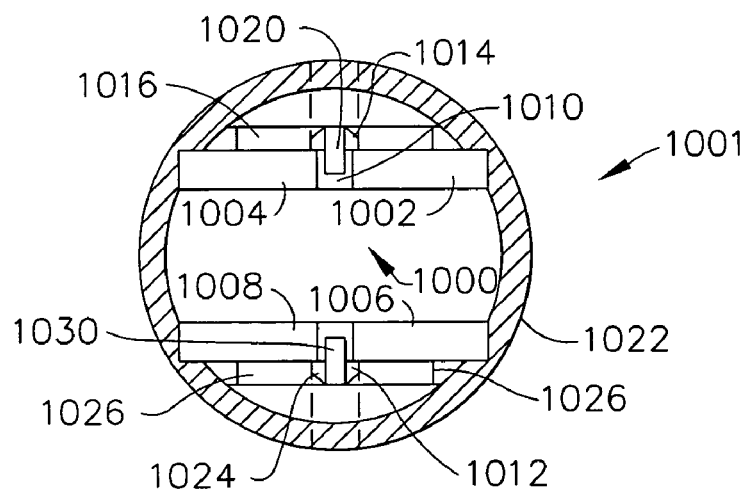
FIG. 31 is a front view in elevation of the single pivot articulation joint of FIG. 30 taken in cross section through upper and lower tip pins from the moment arms and through the EAP stack actuators.
Figure 32:
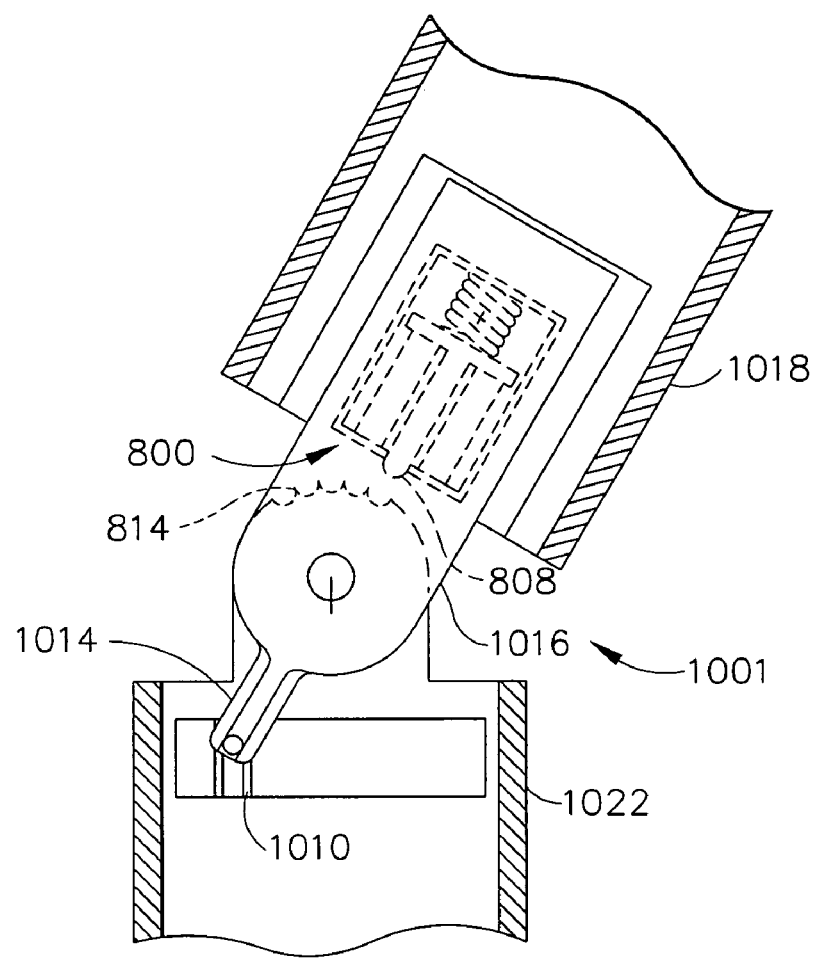
FIG. 32 is a top view of the single pivot articulation joint of FIG. 30 taken in cross section along a top surface of the upper pivot tab of the proximal frame ground after articulation of the distal frame ground to the left but before deenergizing the EAP articulation locking mechanism to effect articulation locking.
Figure 33:
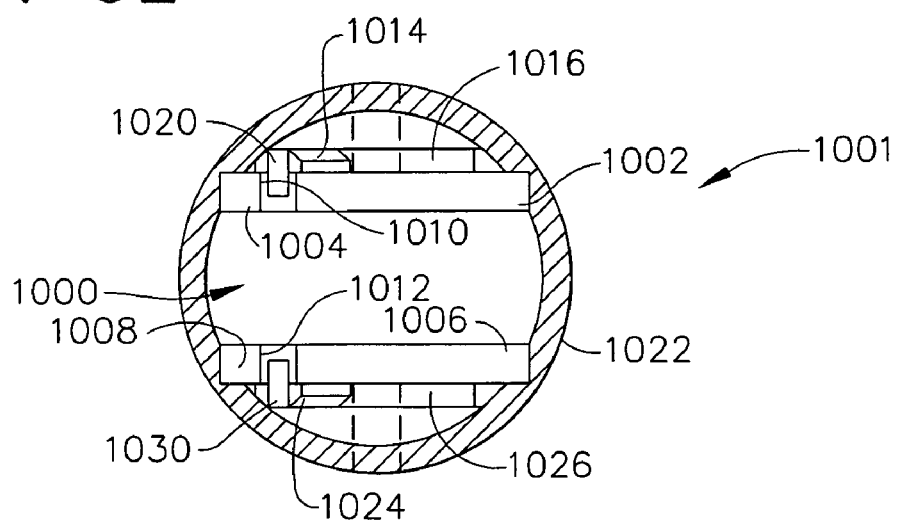
FIG. 33 is a front view in elevation of the single pivot articulation joint of FIG. 31 taken in cross section through the upper and lower tip pins from the moment arms and through the expanded left and compressed right EAP stack actuators.

In FIGS. 30–31, the EAP articulation locking mechanism 800 is activated to disengage the locking tip 808 from the gear segment 814 in preparation for articulation. In FIGS. 32–33, the upper and lower left EAP stack actuators 1002, 1006 have been energized to expand, laterally moving rightward the upper and lower longitudinal tracks 1010, 1012, thereby compressing the upper and lower EAP stack actuators 1004, 1008 and moving distal frame ground 1022 correspondingly against the reaction force from the upper and lower inwardly directed tip pins 1020, 1030, which in the illustrative articulation is to the left.

Surgical Instrument with EAP Actuated Flexneck Articulation Joint.

Figure 34:
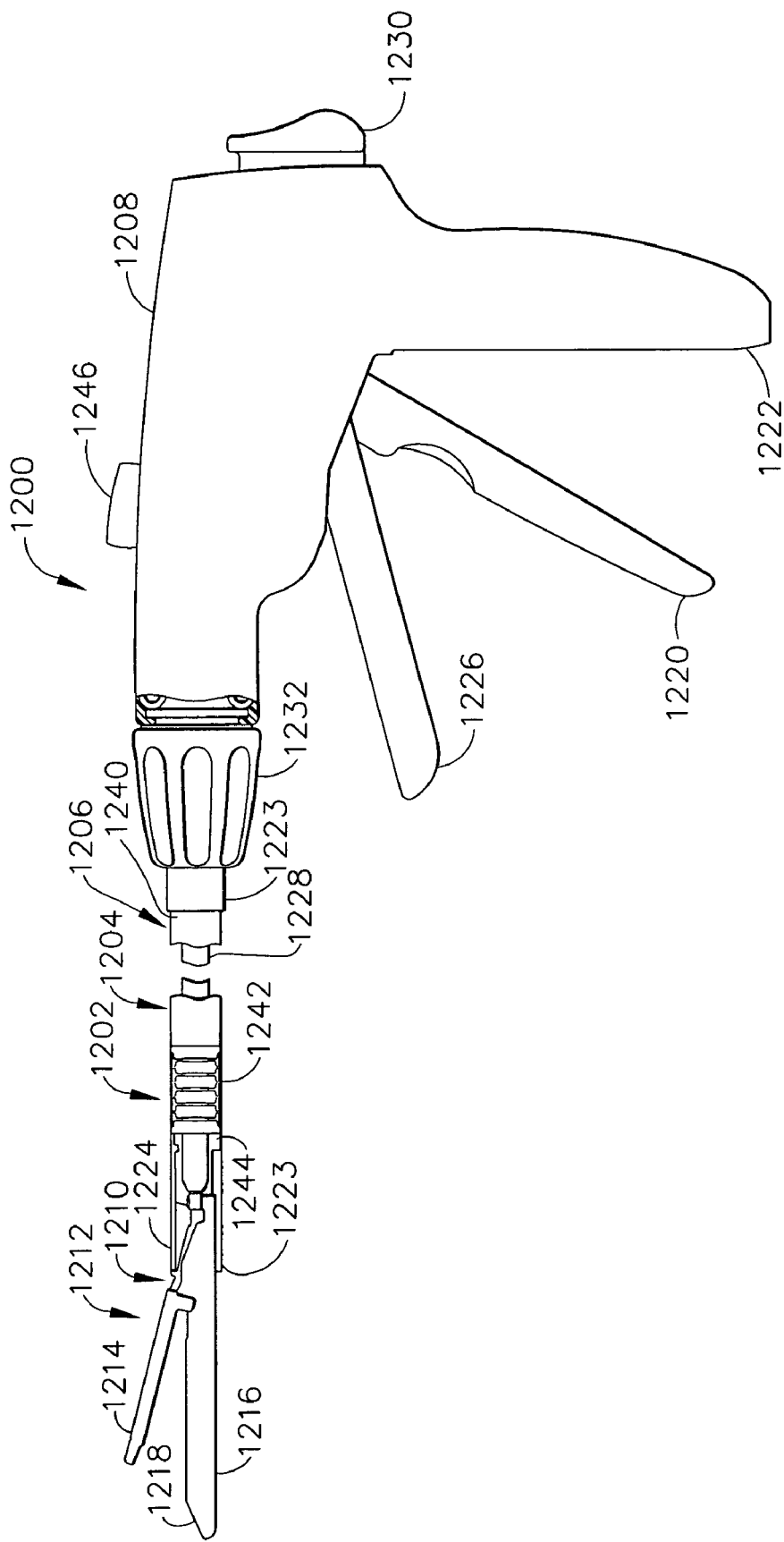
FIG. 34 is a right side view in elevation of a surgical instrument with a closure sleeve assembly cut away to expose an EAP actuated articulation mechanism that articulates a flexible articulating frame ground.

In FIG. 34, a surgical instrument 1200 advantageously incorporates an EAP actuated articulation joint 1202 that is integral to an articulating frame assembly 1204 of an elongate shaft 1206 that transfers separate closure and firing motions from a handle 1208 to an end effector 1210, depicted as a staple applying assembly 1212 having a closeable anvil 1214 that is pivotally attached to an elongate channel 1216 that holds a replaceable staple cartridge 1218. The handle 1208 includes a closure trigger 1220 that is squeezed proximally toward a pistol grip 1222 to effect closure of the anvil 1214. It should be appreciated that a closure sleeve assembly 1223 or other closure means (e.g., EAP actuated anvil, internal longitudinally translating member, etc.) that is not shown acts upon an anvil closure feature 1224 to effect opening and closing of the anvil 1214. Once closed and clamped, a more distal firing trigger 1226 is squeezed toward the pistol grip 1222 to effect firing of a firing member 1228 longitudinally down the elongate shaft 1206 to cause severing of tissue and stapling of the severed ends. Once the firing trigger 1226 is released, a closure release button 1230 is depressed along with a slight depression of the closure trigger 1220 to release clamping components followed by release of the closure trigger 1220 to open the anvil 1214 and allow release of the stapled and severed tissue. A rotation knob 1232 allows selective rotation about a longitudinal axis of the elongate shaft 1206.

Figure 35:
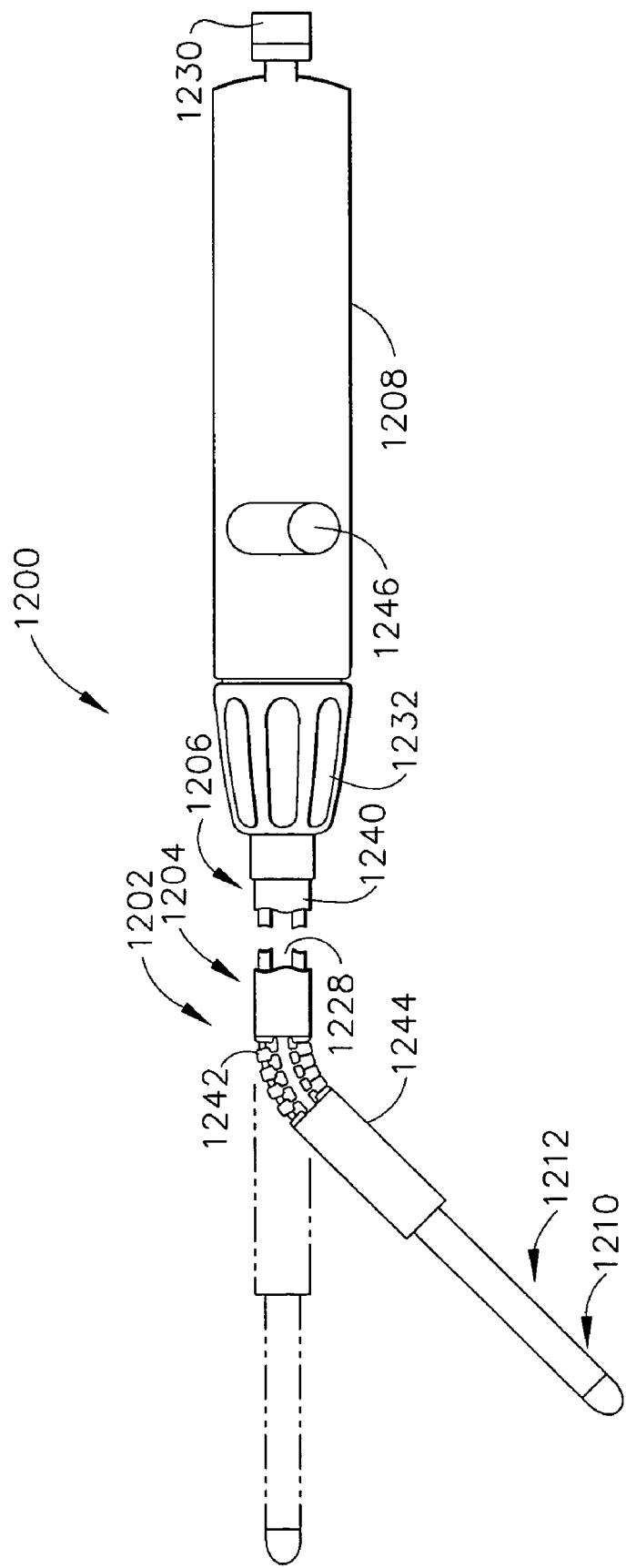
FIG. 35 is a top view of the surgical instrument of FIG. 34 articulating to the left.
Figure 36:
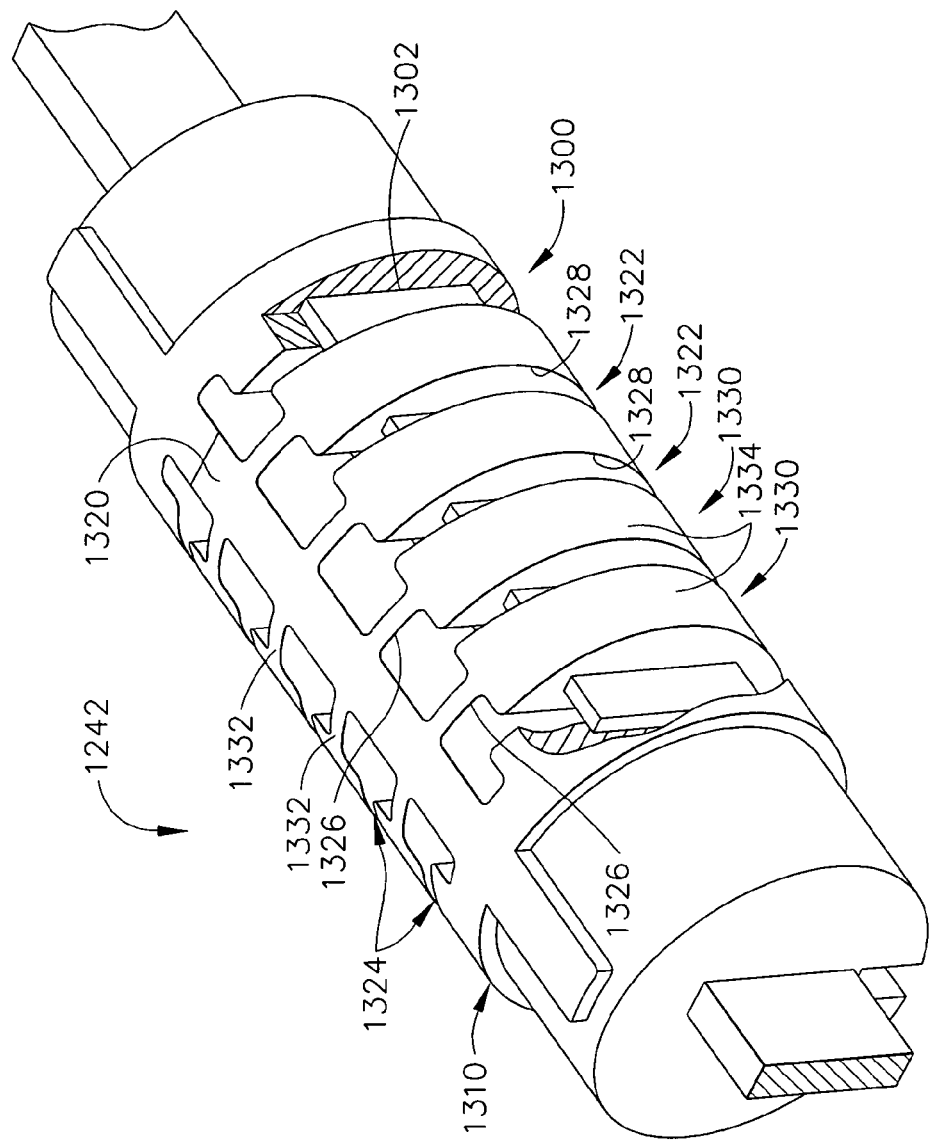
FIG. 36 is a front right perspective view of the articulating frame ground of FIG. 34 that incorporates EAP plate actuators and locking strips.

The articulating frame assembly 1204 includes a proximal frame ground 1240 proximally and rotatably attached to the handle 1208 and distally attached to an articulating frame ground 1242 that in turn is attached to a distal frame ground 1244 that supports the end effector 1210. An articulation control 1246 on the handle 1208 advantageously allows selection of articulation of the articulating frame ground 1242 by activating appropriate electrical signals thereto, such as depicted in FIG. 35 when a leftward articulation has been selected by articulation control 1246. It should be appreciated that the articulation control 1246 may advantageously include manual and/or automatic disengagement of an articulation lock for the articulating frame ground 1242.

In FIGS. 36–39, the articulating frame ground 1242 incorporates an EAP actuating system 1300 that uses left and right EAP plate actuators 1302, 1304 that pass through respective left and rectangular actuator recesses 1306, 1308 (FIGS. 38–39) in each lateral side of a generally cylindrical resilient frame body 1310. A rectangular knife slot 1312 is formed in the resilient frame body 1310 aligned between the left and right rectangular actuator recesses 1306, 1308 for guiding a firing bar 1314 that is a distal portion of the firing member 1228.

Figure 37:
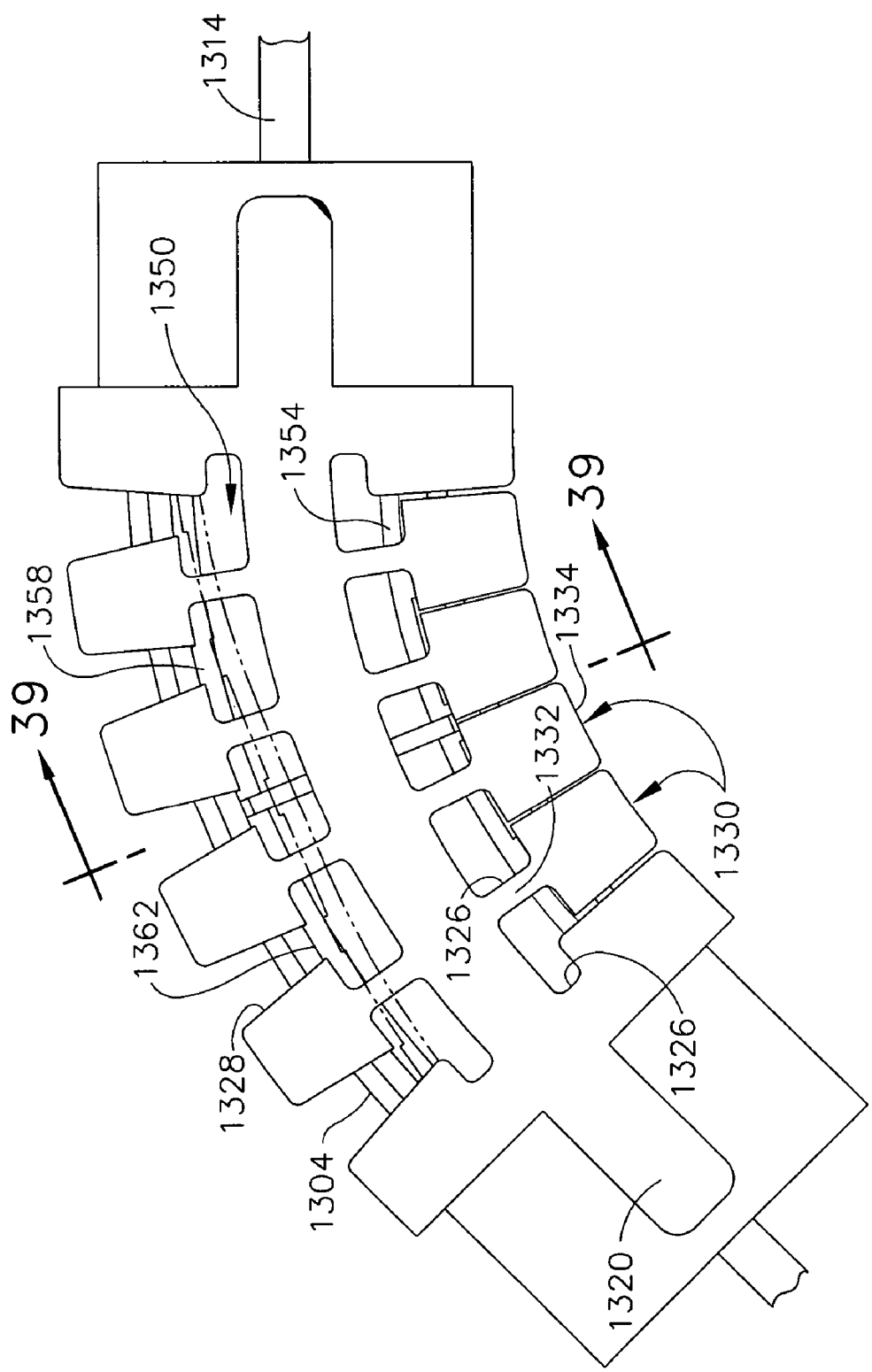
FIG. 37 is a top view of the articulating frame ground of FIG. 34 in a left articulated state with a left EAP locking strip shown in phantom in an unlocked actuated state and a locked relaxed state.

Continuous top and bottom longitudinal bands 1320 (FIGS. 36–37) of the resilient frame body 1310 maintain a longitudinal amount of travel for the firing bar 1314 when the articulating frame ground 1242 is either straight or articulated. The resilient frame body 1310 is advantageously formed from a homogenous material that does not significantly compress along its longitudinal axis. Left and right pluralities of longitudinally aligned vertical recesses 1322, 1324 intersect respectively with the left and right EAP actuator recesses 1306, 1308. Each vertical recess 1322, 1324 includes a rectangular through hole 1326 that passes from top to bottom through the resilient frame body 1310 parallel with and laterally offset from both the rectangular knife slot 1312 and the appropriate one of either the left or right rectangular actuator recess 1306, 1308. Each rectangular through hole 1326 communicates laterally with a narrowed lateral gap 1328. Adjacent vertical recesses 1322, 1324 define therebetween a rib 1330 that has a narrow inner wall 1332, which allows lateral bending of the continuous top and bottom longitudinal bands 1320, and a thicker curved outer slice 1334 that supports the respective one of the EAP plate actuators 1302, 1304 and limits the amount of articulation that may be achieved in that direction before the narrowed lateral gaps 1328 collapse fully as one or both EAP plate actuators 1302, 1304 are activated to bend in a selected direction. In FIG. 37, for instance, the left EAP plate actuator 1302 is activated to actuate to the left with the right EAP plate actuator 1304 stretching in response. It should be appreciated that the left and right EAP plate actuators 1302, 1304 may alternatively contract or expand when electrically activated to create a pull or a push respectively within the left and right rectangular actuator recesses 1306, 1308.

Figure 38:
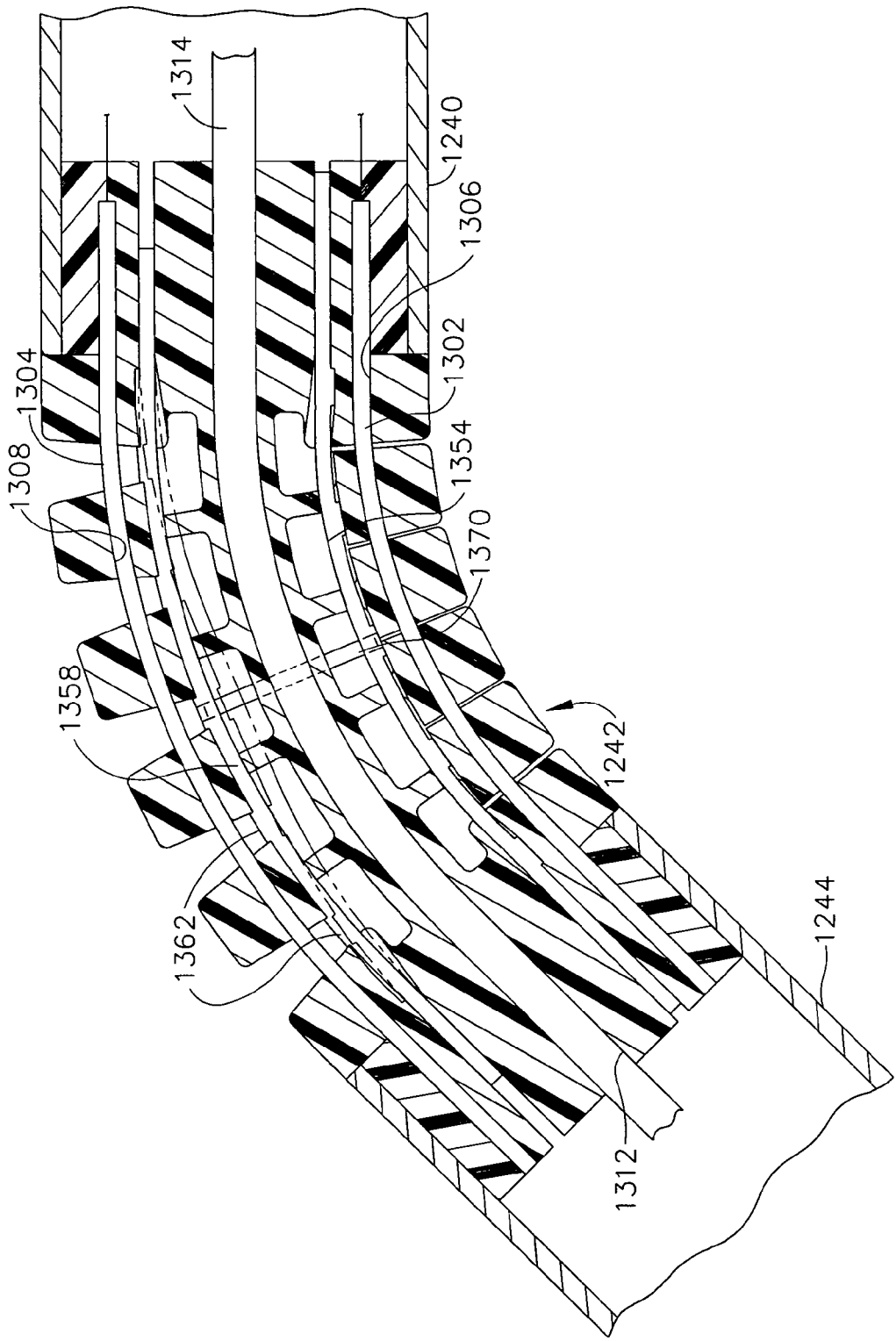
FIG. 38 is a top view of the articulating frame ground of FIG. 34 in a left articulated state taken in cross section through the EAP plate actuators and EAP locking strips.
Figure 39:
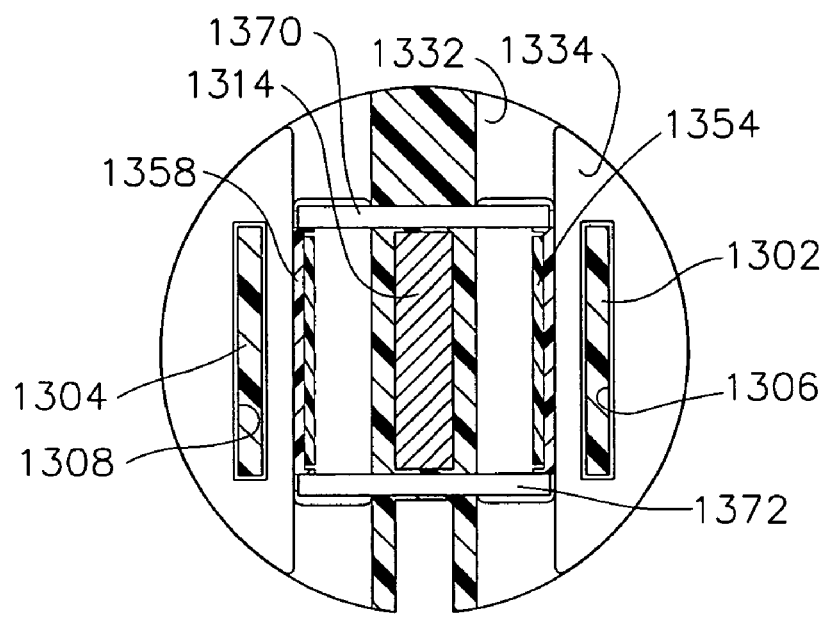
FIG. 39 is a front view in elevation of the articulating frame ground of FIG. 37 taken in cross section through lines 39—39 through the lateral guide pins.

In FIGS. 38–39, the articulating frame ground 1242 advantageously includes an EAP articulation locking mechanism 1350 that selectively holds the resilient frame body 1310 in an articulated left or an articulated right condition. To that end, a left locking passage 1352 is defined passing through the left plurality of rectangular through holes 1326 proximate to their leftmost outer portion, allowing a left ridged EAP locking strip 1354 to pass therethrough. Similarly, a right locking passage 1356 is defined as passing through the right plurality of rectangular through holes 1326 proximate to their rightmost outer portion, allowing placement of a right ridged EAP locking strip 1358. Along their respective outermost surface 1360 of both the left and right ridged EAP locking strips 1354, 1358, a plurality of longitudinally spaced vertical blocking ridges 1362 are longitudinally spaced and sized to define, in conjunction with the geometry of the ribs 1330 to lock at a desired articulation amount. In particular, when the flexible frame ground 1242 articulates toward the opposite side of a respective ridged EAP locking strip 1354, 1358, the ribs 1330 on that side arc away from one another, as depicted in FIG. 38 in articulating to the left. Once the ribs 1330 have reached a spacing sufficient for locking (i.e., wider than the longitudinal width of the vertical blocking ridges 1362, the right ridged EAP locking strip 1358 is biased outwardly to snap its ridges 1362 between adjacent thickened thicker curved outer slices 1334 of adjacent ribs 1330. Activating the right ridged EAP locking strip 1358 causes contraction that unlocks the right ridged EAP locking strip 1358. In FIG. 39, lateral upper and lower guide pins 1370, 1372 that pass above and below the rectangular knife slot 1312 preserve lateral alignment.

Figure 40:
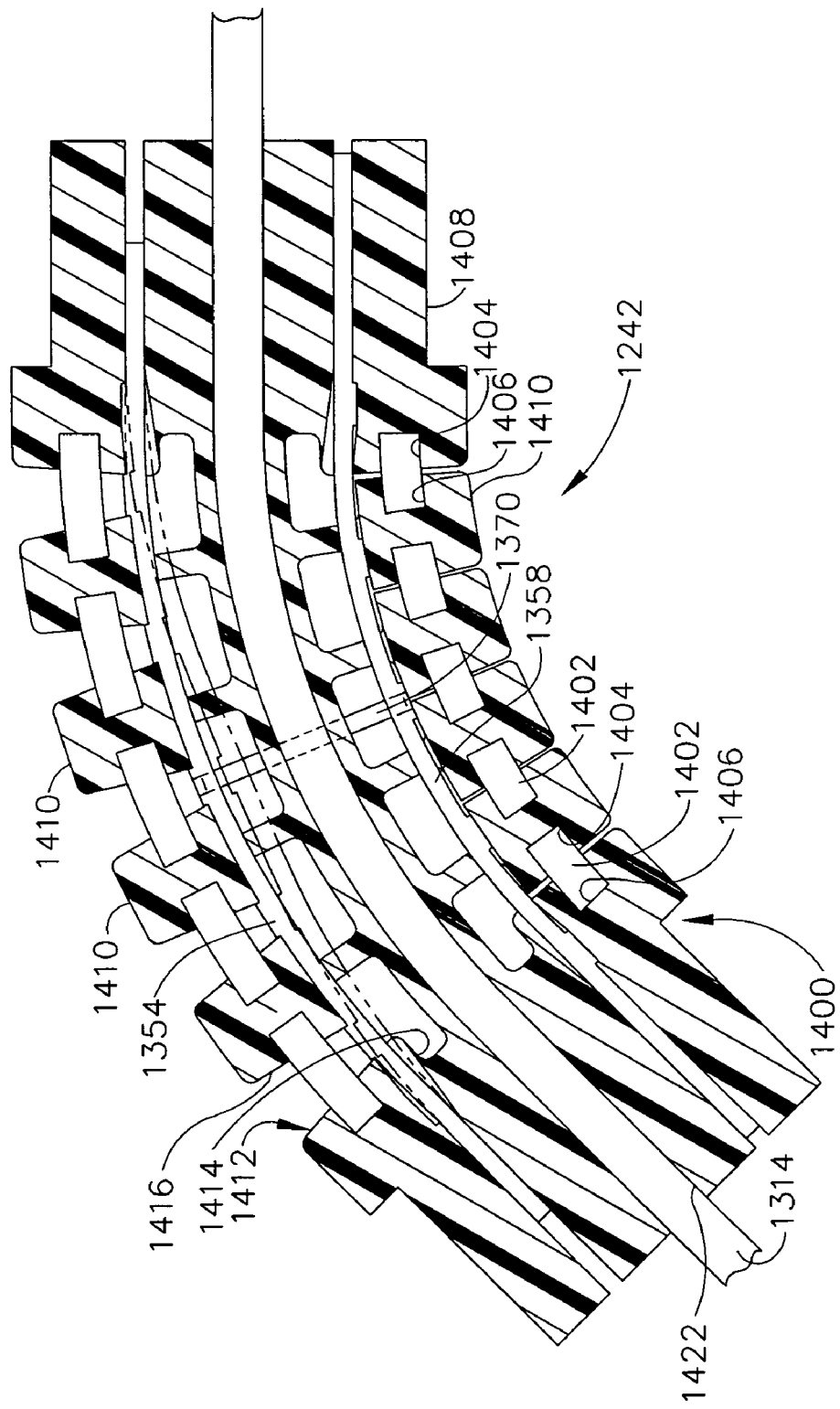
FIG. 40 is a top view of an alternate articulating frame ground taken in cross section through a plurality of EAP rib spreader actuators.

In FIG. 40, the articulating frame ground 1242 incorporates an EAP actuating system 1400 that uses a plurality of left and right EAP rib spreader plate actuators 1402 that each reside between an opposing pair of distally and proximally open rectangular recesses of a resilient frame body 1408. Each opposing pair of distally and proximally open rectangular actuator recesses 1404, 1406 respectively are formed in an adjacent pair (proximal/distal) of laterally defined ribs 1410. Each rib 1410 includes a vertical slot 1412 that is open outwardly laterally along its height with a wider rectangular through hole 1414 more inwardly positioned that narrows into an outer vertical slot 1416. Each rib 1410 thus includes a thin inner wall 1418 that connects to upper and lower longitudinal continuous bands 1420. A rectangular knife slot 1422 is formed laterally along the longitudinal centerline. Left and right ridged EAP locking strips 1354, 1358, as described above, advantageously relax to an expanded curved shape on the expanded side of the articulating frame ground 1242 to lock, with longitudinal alignment maintained by lateral guide pins 1370.

Figure 42:
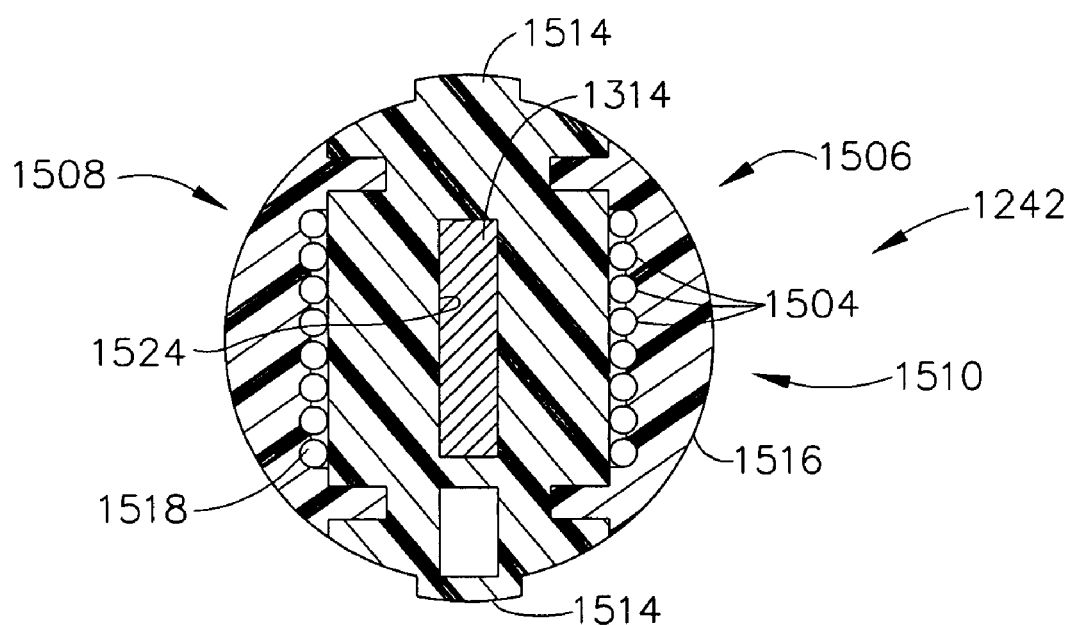
FIG. 42 is a front view in elevation of the additional alternative articulating frame ground of FIG. 41 taken in cross section along lines 42—42.
Figure 41:
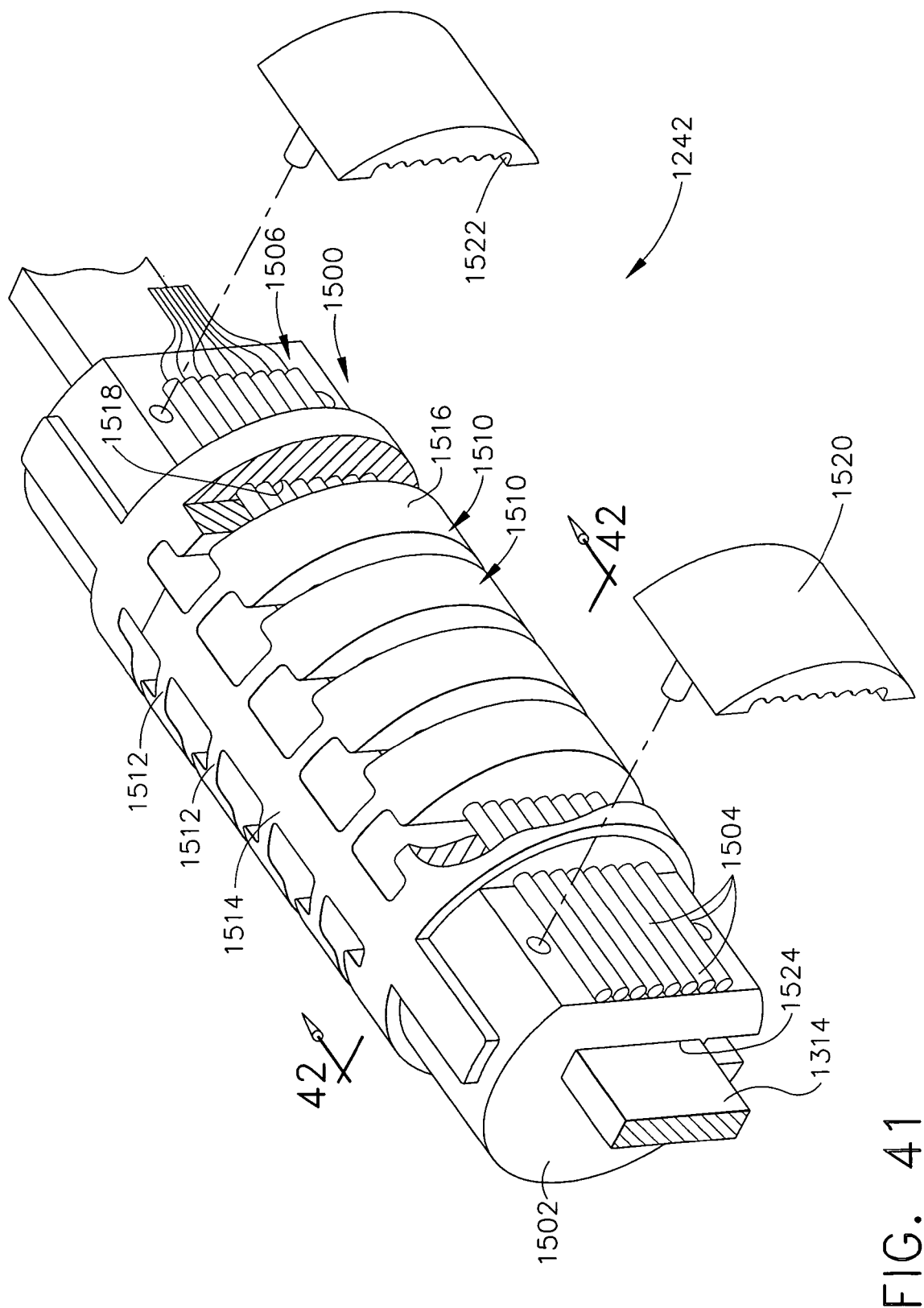
FIG. 41 is a right perspective partially exploded view of an additional alternative articulating frame ground having a plurality of EAP fiber actuators.

In FIGS. 41–42, the articulating frame ground 1242 incorporates a further alternative EAP actuating system 1500 into a resilient frame body 1502 that includes longitudinally aligned EAP fiber actuators 1504 arranged in left and right vertical stacks 1506, 1508 that pass through a respectively left and right plurality of lateral ribs 1510, each having a thin inner vertical wall 1512 that connects to continuous longitudinal top and bottom bands 1514 to facilitate lateral bending thereof. Each rib 1510 widens laterally to a thick outer slice 1516 that is dimensioned for the limitation on articulation to that side. Each thick outer slice 1516 includes a vertical aligned longitudinal through hole 1518 for allowing the EAP fiber actuators 1504 to pass through. Distal and proximal lateral covers 1520, 1522 longitudinally flank the ribs 1510 to cover respective termination ends of the EAP fiber actuators 1504. A laterally centered knife slot 1524 is formed in the resilient frame body 1502 for the firing bar 1314. Contracting a selected vertical stack 1506, 1508 of EAP fiber actuators 1504 causes articulation to that side with the nonactuated vertical stack 1506, 1508 passively elongating in response thereto.

EAP Support Plates for Firing Bar.

With regard to FIGS. 43–54, lateral symmetry prevails for various versions of pairs of support plate that support a firing bar in an articulation joint. In addition, it is contemplated that applications consistent with the present invention may include either end as the proximal or distal end of a depicted articulation joint for those that are not also longitudinally symmetric. Thus, designation of one laterally symmetric component with a suffix "a" and the designation of a mirror image component with a suffix "b" is not intended to imply either right or left.

Figure 43:
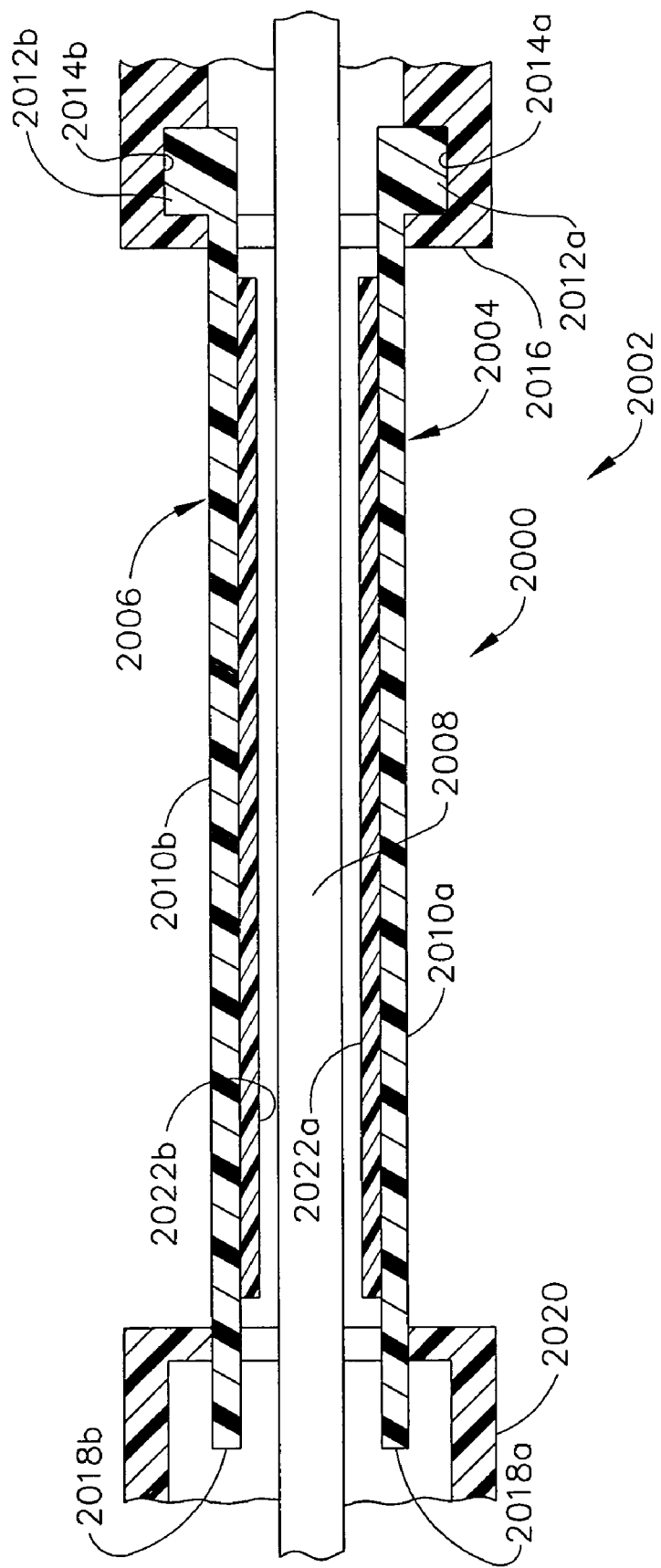
FIG. 43 is a top view taken in longitudinal cross section of a firing bar passing through an articulation joint of a surgical instrument with the firing bar advantageously laterally guided by support plates of inwardly actuated EAP plate actuators with one sliding end.

In FIG. 43, an articulation joint 2000 for a surgical instrument 2002 includes a pair of EAP support plates 2004, 2006 that laterally support a firing bar 2008 to minimize binding and buckling when articulated. Each support plate 2004, 2006 includes a respective structural member 2010a, 2010b (e.g., rigid polymer, metal) that includes a laterally widened end 2012a, 2012b that is captured within a correspondingly sized recess 2014a, 2014b in a first frame ground 2016 and a straight end 2018a, 2018b that is slidingly received within a second frame ground 2020. A longitudinally expansive EAP laminate 2022a, 2022b covers an internal surface of each support plate 2004, 2006.

Figure 44:
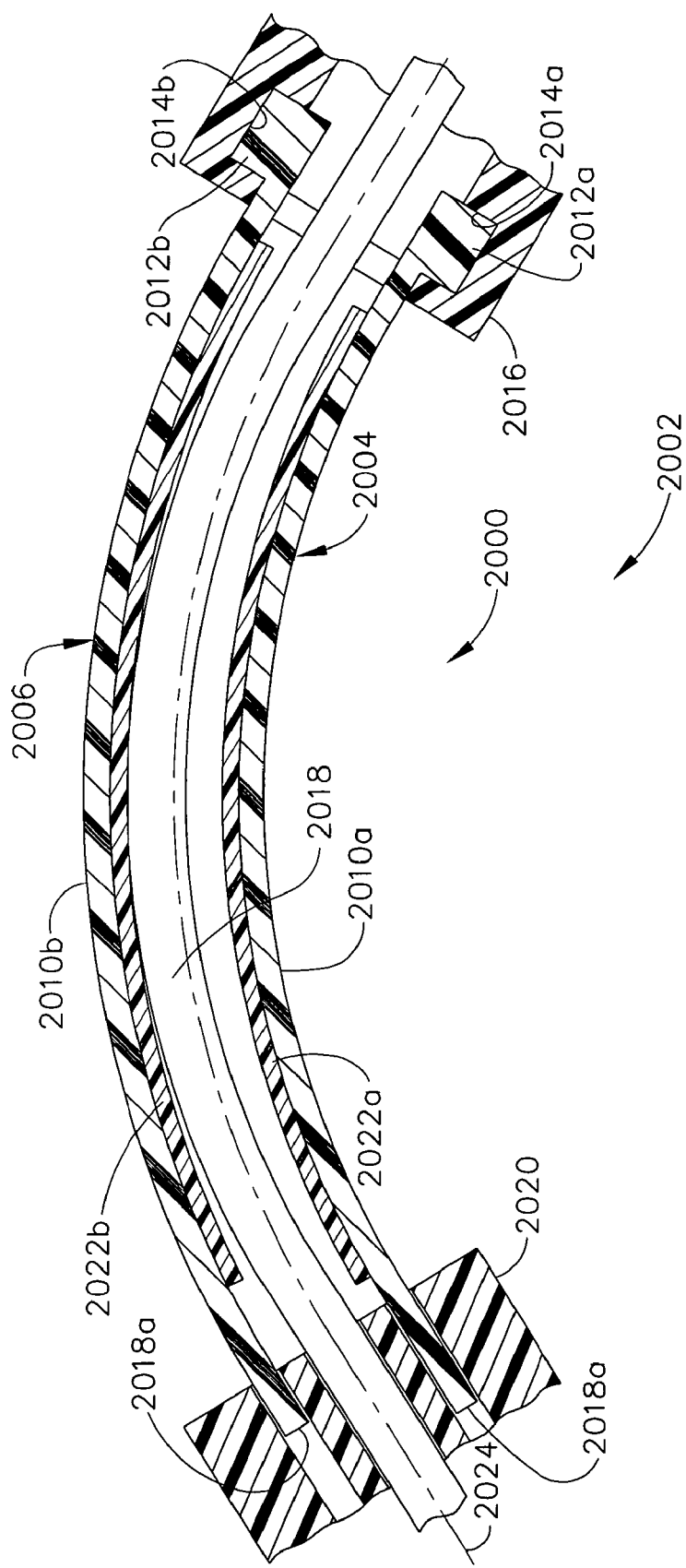
FIG. 44 is a top view taken in longitudinal cross section of the firing bar passing through an articulated articulation joint of the surgical instrument of FIG. 43.

In FIG. 44, the articulation joint 2000 is articulated to one lateral side, causing the firing bar 2008 to overshoot an articulated longitudinal axis 2024 and come into contact with support plate 2006. Lateral support therefrom prevents a blow out of the firing bar 2008 out of the articulation joint 2000 and/or allows fabrication of a more flexible firing bar 2008 with thus reduced force to articulate. In addition, the EAP laminates 2022a, 2022b on each support plate 2004, 2006 are activated as necessary to control the amount of curvature of both to preserve a desired spacing therebetween for the firing bar 2008. The straight ends 2018a, 2018b slide in the second frame ground portion 2020 to accommodate the reduced travel required of the inner support plate 2004 as compared to the outer support plate 2006. The EAP laminate 2022b may further provide cushioning and low surface friction characteristics that assist in laterally guiding the firing bar 2008.

Figure 45:
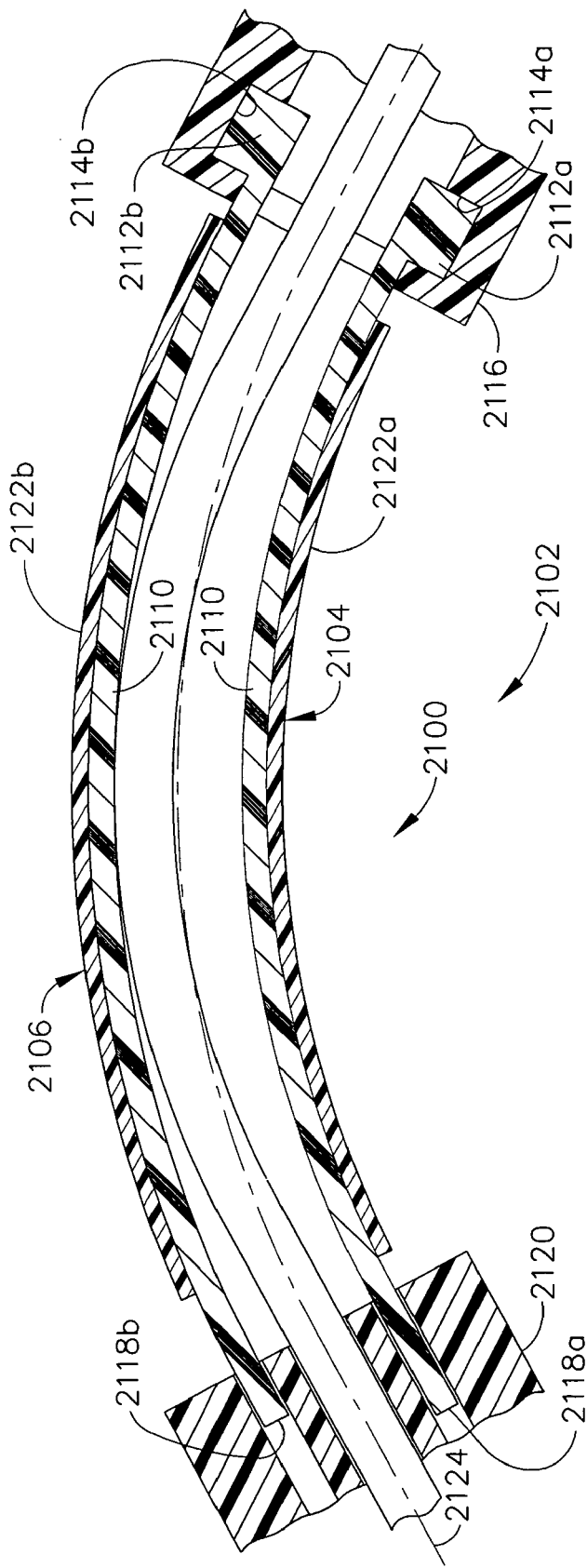
FIG. 45 is a top view taken in longitudinal cross section of a firing bar passing through an articulated articulation joint of a surgical instrument with the firing bar advantageously laterally guided by support plates of outwardly actuated EAP plate actuators with one sliding end.

In FIG. 45, an alternative articulation joint 2100 for a surgical instrument 2102 includes a pair of EAP support plates 2104, 2106 that laterally support a firing bar 2108 to minimize binding and buckling when articulated. Each support plate 2104, 2106 includes, respectively, a structural member 2110a, 211b (e.g., rigid polymer, metal) that includes a laterally widened end 2112a, 2112b that is captured within a correspondingly sized recess 2114a, 2114b in a first frame ground 2116 and a straight end 2118a, 2118b that is slidingly received within a second frame ground 2120. A longitudinally expansive EAP laminate 2122a, 2122b covers an outer surface of each support plate 2104, 2106. The articulation joint 2100 is articulated to one lateral side, causing the firing bar 2108 to overshoot an articulated longitudinal axis 2124 and come into contact with support plate 2106. Lateral support therefrom prevents a blow out of the firing bar 2108 out of the articulation joint 2100 and/or allows fabrication of a more flexible firing bar 2108 with thus reduced force to articulate. In addition, the EAP laminates 2122a, 2122b on each support plate 2104, 2106 respectively are activated as necessary to control the amount of curvature of both to preserve a desired spacing therebetween for the firing bar 2108. The straight ends 2118a, 2118b slide in the second frame ground portion 2120 to accommodate the reduced travel required of the inner support plate 2104 as compared to the outer support plate 2106. Placement of the EAP laminates 2122a, 2122b away from contact with the firing bar 2108 may have advantages such as reducing wear to the EAP laminates 2122a, 2122b.

Figure 46:
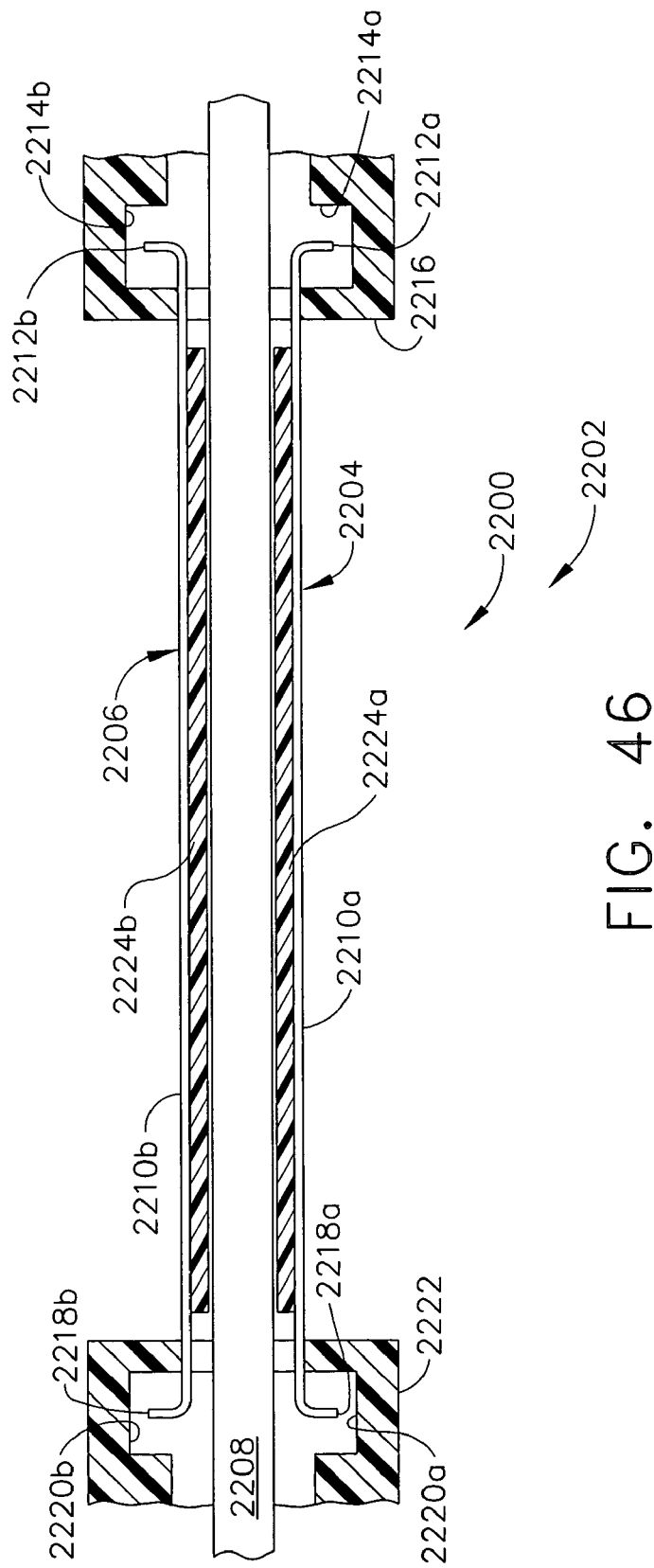
FIG. 46 is a top view taken in longitudinal cross section of a firing bar passing through an articulation joint of a surgical instrument with the firing bar advantageously laterally guided by outwardly actuated EAP support plates having constrained but longitudinally floating hooked ends.

In FIG. 46, an additional alternative articulation joint 2200 for a surgical instrument 2202 includes a pair of EAP support plates 2204, 2206 that laterally support a firing bar 2208 to minimize binding and buckling when articulated. Each support plate 2204, 2206 includes a respective structural member 2210 (e.g., metal) that includes a first outwardly tabbed end 2212a, 2212b that is constrained and longitudinally free floating within a first inwardly open recess 2214a, 2214b in a first frame ground 2216 and a second outwardly tabbed end 2218a, 2218b that is constrained and longitudinally free floating within a second inwardly open recess 2220a, 2220b of a second frame ground 2222. A longitudinally expansive EAP laminate 2224a, 2224b covers an inner surface of each support plate 2204, 2206.

Figure 47:
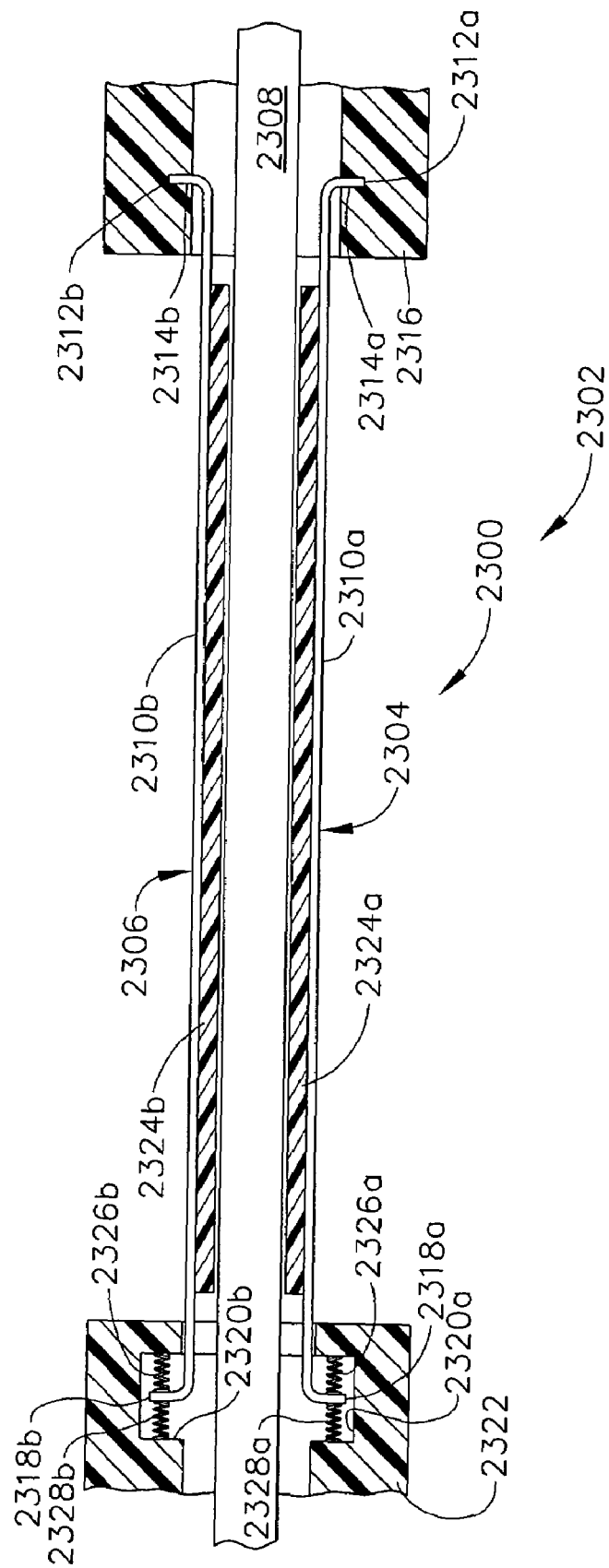
FIG. 47 is a top view taken in longitudinal cross section of a firing bar passing through an articulation joint of a surgical instrument with the firing bar advantageously laterally guided by outwardly actuated EAP support plates, each having one fixed hooked end and one end springedly longitudinally constrained.

In FIG. 47, yet an additional alternative articulation joint 2300 for a surgical instrument 2302 includes a pair of EAP support plates 2304, 2306 that laterally support a firing bar 2308 to minimize binding and buckling when articulated. Each support plate 2304, 2306 includes a respective structural member 2310a, 2310b (e.g., metal) that includes a first outwardly tabbed end 2312a, 2312b that is fixed with an inwardly open slot 2314a, 2314b in a first frame ground 2316 and a second outwardly tabbed end 2318a, 2318b that is constrained and longitudinally free floating within an inwardly open recess 2320a, 2320b of a second frame ground 2322. A longitudinally expansive EAP laminate 2324a, 2324b covers an inner surface of each support plate 2304, 2306. A pair of compression springs 2326a, 2328a are longitudinally aligned within the inwardly open recess 2320a biasing the second outwardly tabbed end 2318a of support plate 2304 to a neutral position therein. Similarly, a pair of compression springs 2326b, 2328b are longitudinally aligned within the inwardly open recess 2320b biasing the second outwardly tabbed end 2318b of support plate 2306 to a neutral position therein.

Figure 48:
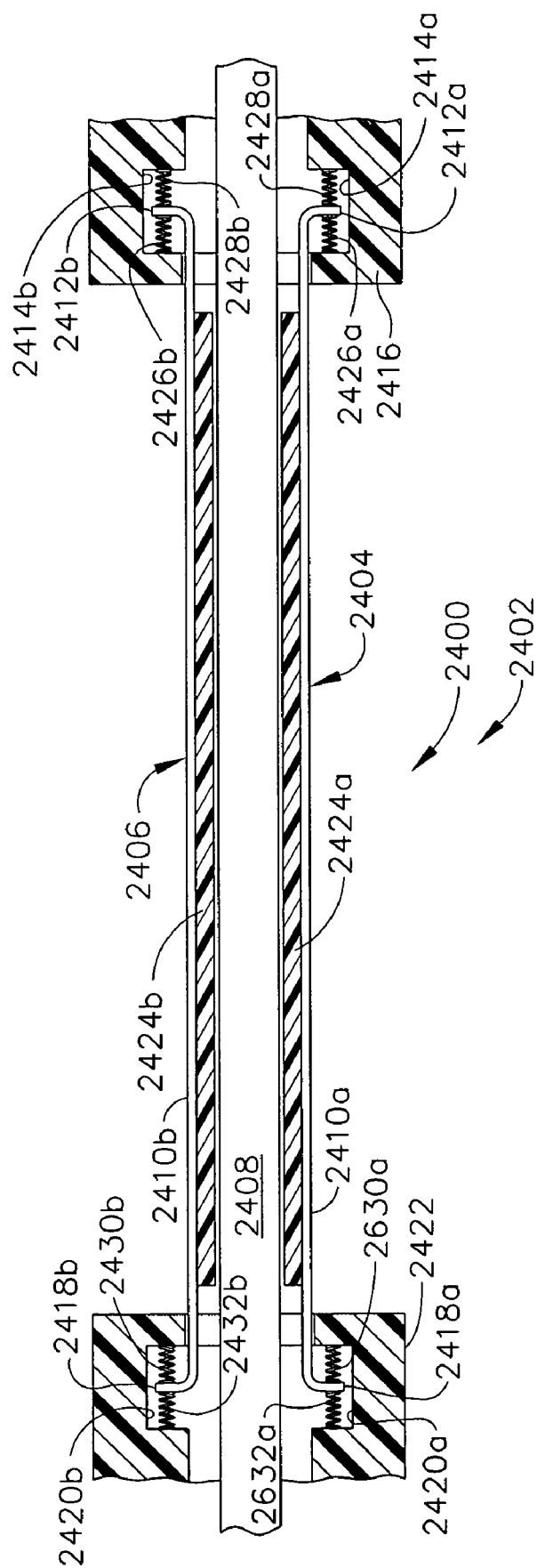
FIG. 48 is a top view taken in longitudinal cross section of a firing bar passing through an articulation joint of a surgical instrument with the firing bar advantageously laterally guided by outwardly actuated EAP support plates with each having both ends springedly longitudinally constrained.

In FIG. 48, yet a further alternative articulation joint 2400 for a surgical instrument 2402 includes a pair of EAP support plates 2404, 2406 that laterally support a firing bar 2408 to minimize binding and buckling when articulated. Each support plate 2404, 2406 includes, respectively, a structural member 2410a, 2410b (e.g., metal) that includes a first outwardly tabbed end 2412a, 2412b that is constrained but longitudinally free floating with a first inwardly open recess 2414a, 2414b in a first frame ground 2416a, 2416b and a second outwardly tabbed end 2418a, 2418b that is constrained and longitudinally free floating within a second inwardly open recess 2420a, 2420b of a second frame ground 2422. A longitudinally expansive EAP laminate 2424a, 2424b covers an inner surface of each support plate 2404, 2406. A respective pair of compression springs 2426a–2428a, 2426b–2428b are longitudinally aligned respectively within the first inwardly open recess 2414a, 2414b biasing the first outwardly tabbed end 2412a, 2412b of each support plate 2404, 2406 to a neutral position therein. Another respective pair of compression springs 2430a–2432a, 2430b–2432b are longitudinally aligned within the second inwardly open recess 2420a, 2420b biasing the second outwardly tabbed end 2418a, 2418b of each support plate 2404, 2406 to a neutral position therein.

Figure 51:
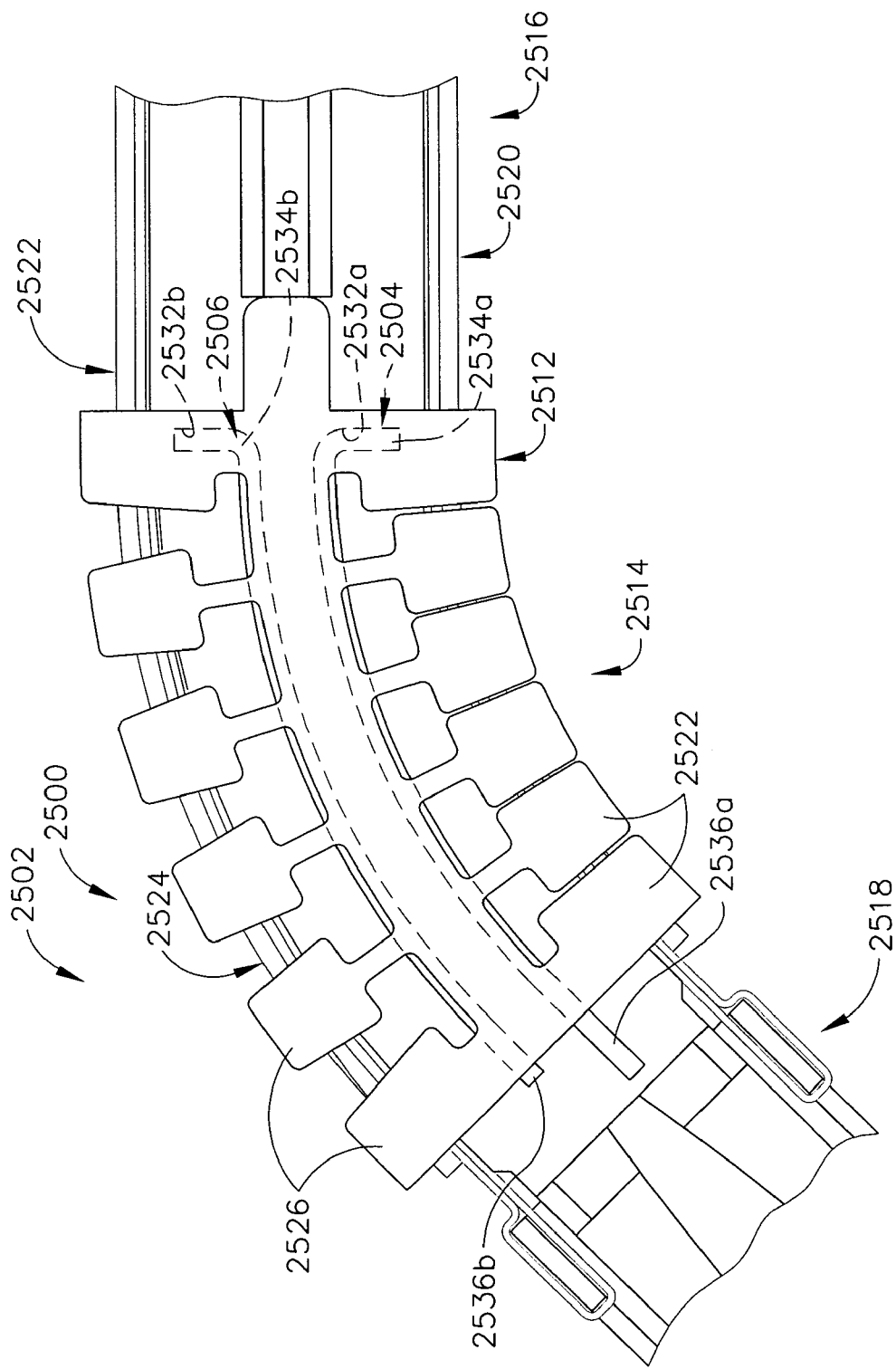
FIG. 51 is a top view of the flexible articulation joint of FIG. 49 articulated to the left.
Figure 52:
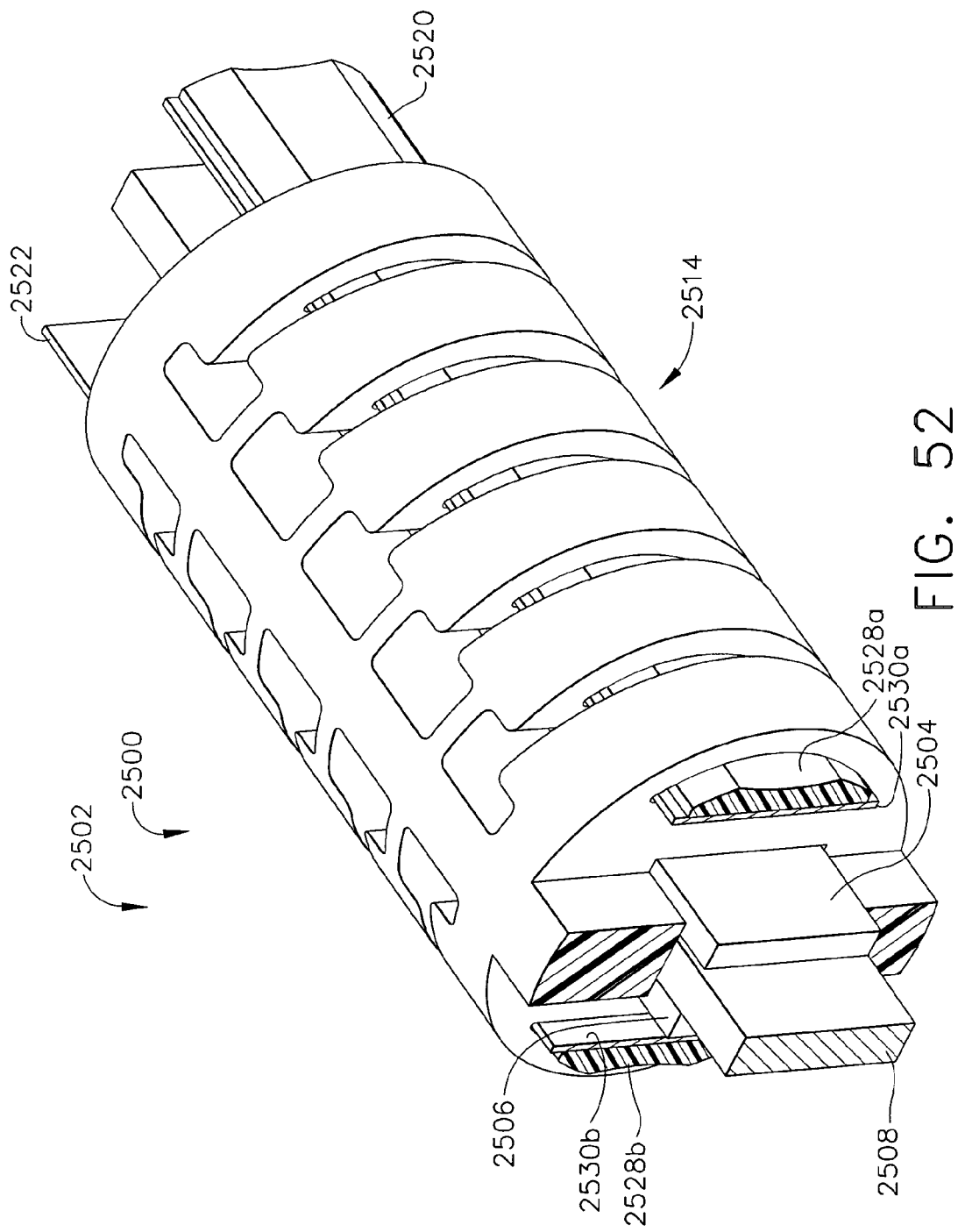
FIG. 52 is a front right perspective view of a flexible articulation joint incorporating EAP support plates of FIG. 45 or 46 and also including left and right EAP plate articulation actuators.

In FIGS. 49–52, yet a further alternative articulation joint 2500 for a surgical instrument 2502 incorporates EAP support plates 2504, 2506 that reside on each lateral side of a firing bar 2508 in a knife slot 2510 of a resilient frame body 2512 of an articulating frame ground 2514 proximally coupled to a proximal frame ground 2516 and distally coupled to a distal frame ground 2518. A left EAP plate actuator 2520 passes through a left plurality of lateral ribs 2522 formed in the resilient frame body 2512. A right EAP plate actuator 2524 passes through a right plurality of lateral ribs 2526. Each EAP plate actuator 2520, 2524 which extends proximally into the proximal frame ground 2516, includes, respectively, an outer EAP laminate layer 2528a, 2528b attached to an inner plate 2530a, 2530b and is configured to actuate when electrically energized to bend the distal frame round 2518 toward the other side. The resilient frame body 2512 includes proximal inwardly open recesses 2532 that grip respective proximal, outwardly curved ends 2534a, 2534b of each support plate 2504, 2506. Distal straight ends 2536a, 2536b of each support plate 2504, 2506 are allowed to slide out of the knife slot 2510 to adjust for changes in travel for articulation, as depicted in FIG. 51.

Figure 53:
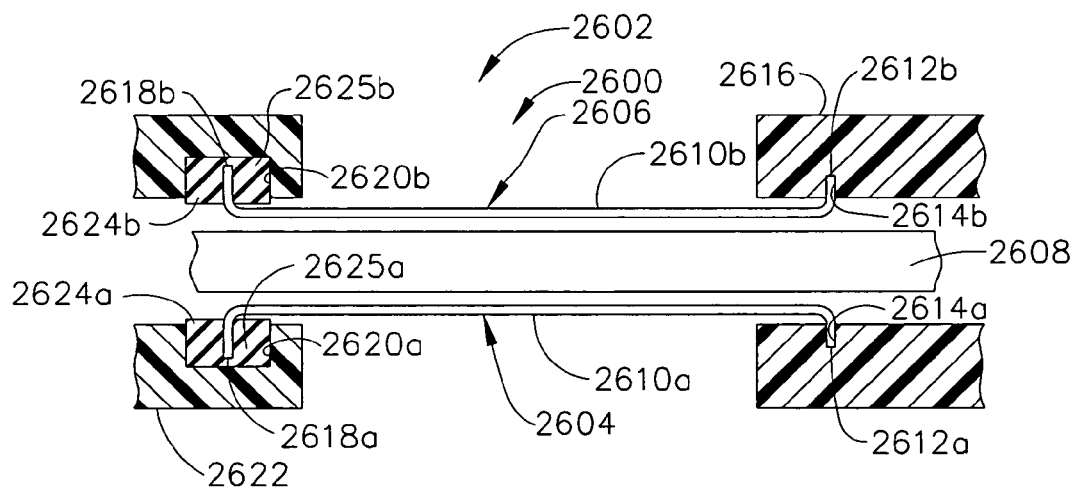
FIG. 53 is a top view of an articulation joint taken in cross section through a longitudinal axis with a pair of support plates having one outwardly bent end fixed on one side of the joint and having another outwardly bent end resiliently held within a frame recess between opposing EAP stack actuators.

In FIG. 53, yet another alternative articulation joint 2600 for a surgical instrument 2602 includes a pair of EAP support plates 2604, 2606 that laterally support a firing bar 2608 to minimize binding and buckling when articulated. Each support plate 2604, 2606 includes a respective structural member 2610 (e.g., metal, resin, polymer) that includes a first outwardly tabbed end 2612 that is fixed with a respective right and left inwardly open slot 2614a, 2614b in a first frame ground 2616 and a second outwardly tabbed end 2618a, 2618b that is respectively constrained and longitudinally free floating within an inwardly open recess 2620a, 2620b of a second frame ground 2622.

An outer longitudinally expansive EAP laminate 2624a, 2624b is positioned in an outer portion of the respective inwardly open recess 2620a, 2620b against the second outwardly tabbed end 2618a, 2618b. An inner longitudinally expansive EAP laminate 2625a, 2625b is positioned in an inner portion of the inwardly open recess 2620a, 2620b against a respective opposite side of the second outwardly tabbed end 2618a, 2618b. Thus, activating one of the outer longitudinal expansive EAP laminate 2624a, 2624b effectively lengthens the respective support plate 2604, 2606. Conversely, activating one of the inner longitudinal expansive EAP laminate 2625a, 2625b effectively shortens the respective support plate 2604, 2606.

Figure 54:
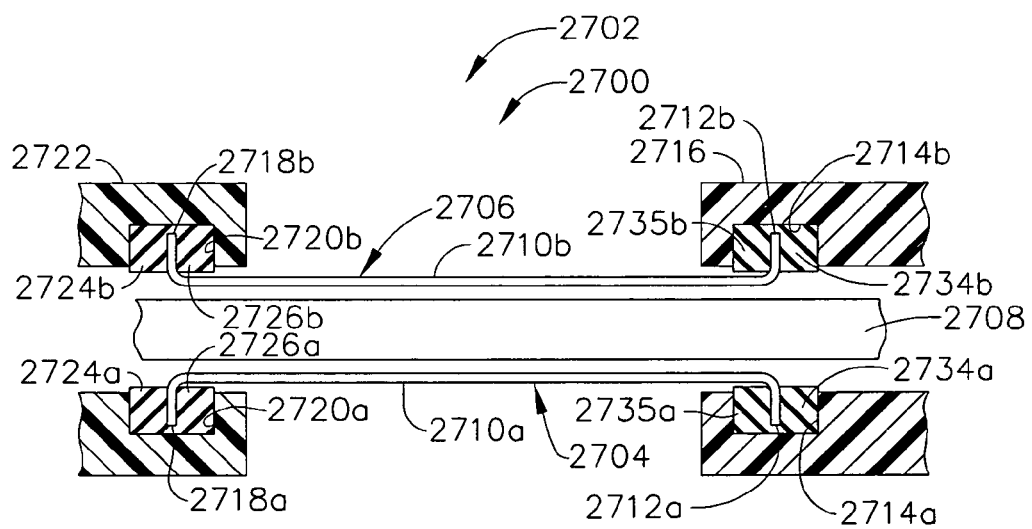
FIG. 54 is a top view of an articulation joint taken in cross section through a longitudinal axis with a pair of support plates having both outwardly bent ends resiliently held within respective frame recesses between opposing EAP stack actuators.

In FIG. 54, yet a further alternative articulation joint 2700 for a surgical instrument 2702 includes a pair of EAP support plates 2704, 2706 that laterally support a firing bar 2708 to minimize binding and buckling when articulated. Each support plate 2704, 2706 includes a respective structural member 2710a, 2710b (e.g., metal) that includes a first outwardly tabbed end 2712a, 2712b that is constrained but longitudinally free floating with a first inwardly open recess 2714a, 2714b in a first frame ground 2716 and a second outwardly tabbed end 2718a, 2718b that is constrained and longitudinally free floating within a second inwardly open recess 2720a, 2720b of a second frame ground 2722.

An outer longitudinally expansive EAP laminate 2724a, 2724b is positioned in an outer portion of the respective second inwardly open recess 2720a, 2720b against the second outwardly tabbed end 2718a, 2718b. An inner longitudinally expansive EAP laminate 2725a, 2725b is positioned in an inner portion of the second inwardly open recess 2720a, 2720b against a respective opposite side of the second outwardly tabbed end 2618a, 2618b. To effectively double the effective lengthening or shortening of the support plate 2704, 2706, another outer longitudinally expansive EAP laminate 2734a, 2734b is positioned in an outer portion of the respective first inwardly open recess 2714a, 2714b against the first outwardly tabbed end 2712a, 2712b. Another inner longitudinally expansive EAP laminate 2735a, 2735b is positioned in an inner portion of the first inwardly open recess 2720a, 2720b against a respective opposite side of the first outwardly tabbed end 2612a, 2612b. Thus, activating a first lateral pair of the outer longitudinal expansive EAP laminate 2724a, 2734a effectively lengthens the support plate 2704 and activating the second lateral pair of the outer longitudinal expansive EAP laminate 2724b, 2734b effectively lengthens the support plate 2706. Conversely, activating a first lateral pair of the inner longitudinal expansive EAP laminate 2726a, 2736a effectively shortens the support plate 2704 and activating the second lateral pair of the inner longitudinal expansive EAP laminate 2726b, 2736b effectively shortens the support plate 2706.

In each of these versions, articulation support control circuitry may advantageously activate one or both EAP support plates to effect their longitudinal length and/or to effect their degree of longitudinal deflection or bending. For example, activation of the EAP support plates may occur to effect articulation of the joint and to support the firing bar, and thus remain active. As another example, actuation of the articulation joint may be performed separately by mechanical or electrical means with articulation support control circuitry activated while actuated or immediately proceeding firing (e.g., once closing of the end effector is sensed or commanded).

While the present invention has been illustrated by description of several embodiments and while the illustrative embodiments have been described in considerable detail, it is not the intention of the applicant to restrict or in any way limit the scope of the appended claims to such detail. Additional advantages and modifications may readily appear to those skilled in the art.

For example, while a hand manipulated surgical instrument is depicted in illustrative versions, it should be appreciated that aspects of the present invention may be incorporated into robotically positioned and controlled instruments. Thus a handle portion may comprise an external portion that is stabilized in a fixture.

What is claimed is:

1. A surgical instrument, comprising:
   a handle portion comprising:
     articulation control circuitry operably configured to produce an articulation support signal,
     a firing mechanism including a longitudinally translating firing bar;
   an elongate shaft attached to the handle and including a firing bar guide slot encompassing the firing bar; and
   an end effector distally attached to the elongate shaft and actuated by a distal end of the firing bar;
   an articulation joint coupling the elongate shaft to the end effector and in communication with the articulation support signal through the elongate shaft; and
   a pair of electroactive polymer support members positioned in the articulation joint on each lateral side of the firing bar responsive to the articulation support signal to dimensionally adjust in compensation for articulating to a selected lateral side.

2. The surgical instrument of claim 1, wherein a selected one of the pair of electroactive polymer support members on an inside of an articulation movement contracts in response to the articulation support signal.

3. The surgical instrument of claim 1, wherein a selected one of the pair of electroactive polymer support members on an outside of an articulation movement elongates in response to the articulation support signal.

4. The surgical instrument of claim 1, wherein the electroactive polymer support members each comprise an electroactive polymer plate actuator operably configured to laterally deflect in response to the articulation support signal.

5. The surgical instrument of claim 4, wherein a selected one of the proximal portion and the distal portion of the articulation joint include a frame recess communicating with the firing bar guide slot, each electroactive polymer plate actuator comprising a rigid substrate having an outwardly deflected end received in the frame recess and comprising an electroactive polymer actuator attached to one side of the rigid substrate to effect bending in response to the articulation support signal.

6. The surgical instrument of claim 5, further comprising a resilient member inserted in longitudinal opposition between the outwardly deflected end of the rigid substrate and a wall of the frame recess.

7. The surgical instrument of claim of claim 5, wherein the electroactive polymer actuator is attached on an inside surface of the rigid substrate proximate to the firing bar.

8. The surgical instrument of claim 5, wherein an inner surface of the rigid substrate is proximate to the firing bar and wherein the electroactive polymer actuator is attached on an outer surface of the rigid substrate.

9. The surgical instrument of claim 1, wherein the articulation joint comprises a proximal portion attached to the elongate shaft and a distal portion attached to the end effector, the proximal portion attached for articulating movement to the distal portion, each electroactive polymer actuator attached respectively to the proximal portion and distal portion and operatively configured to effect articulation in response to the articulation support signal.

10. The surgical instrument of claim 9, wherein the articulation joint comprises the proximal portion pivotally attached to the distal portion.

11. The surgical instrument of claim 9, wherein the articulation joint comprises an upper band and a lower band each formed of a flexible and longitudinally incompressible material attached between the proximal and distal portions and a plurality of left vertical ribs and a plurality of right vertical ribs, each rib connected on a respective lateral side between the upper and lower bands.

12. The surgical instrument of claim 9, wherein a selected one of the pair of electroactive polymer support members on an inside of an articulation movement contracts in response to the articulation support signal.

13. The surgical instrument of claim 9, wherein a selected one of the pair of electroactive polymer support members on an outside of an articulation movement elongates in response to the articulation support signal.

14. The surgical instrument of claim 9, wherein the electroactive polymer support members each comprise an electroactive polymer plate actuator operably configured to laterally deflect in response to the articulation support signal.

15. The surgical instrument of claim 9, wherein each of the electroactive polymer support members comprise a structural member having a longitudinal portion and an outwardly bent tab at each end constrained respectively within the proximal portion and the distal portion of the articulation joint, and further comprise an inner and outer electroactive polymer actuator, each configured for longitudinal expansion positioned on longitudinally opposite sides of a selected one of the outwardly bent tabs wherein the respective portion of the articulation joint includes an inwardly open recess that receives the inner and outer electroactive polymer actuators and the selected one of the outwardly bent tabs.

16. The surgical instrument of claim 15, wherein each of the electroactive polymer support members further comprise a second pair of inner and outer electroactive polymer actuators each configured for longitudinal expansion positioned on longitudinally opposite sides of the other one of the outwardly bent tabs wherein the respective portion of the articulation joint includes an inwardly open recess that receives the second pair of inner and outer electroactive polymer actuators and the other one of the outwardly bent tabs, the articulation control circuitry operatively configured to activate both outer electroactive polymer actuators of a selected electroactive polymer support member to effect lengthening and to activate both inner electroactive polymer actuators to effect shortening.

17. A surgical instrument, comprising:

a handle portion comprising an articulation control circuitry operably configured to produce an articulation support signal;

an elongate shaft attached to the handle portion; and an end effector distally attached to the elongate shaft;

an articulation joint coupling the elongate shaft to the end effector and in communication with the articulation support signal through the elongate shaft; and a pair of electroactive polymer support members positioned on lateral sides of the articulation joint, each having one end longitudinally constrained therein and the other slidingly received, aligned with and offset from a longitudinal axis of the elongate shaft, each electroactive polymer support member responsive to the articulation support signal to bend laterally.

* * * * *